US012784917B1

(12) United States Patent
Isbell

(10) Patent No.: US 12,784,917 B1
(45) Date of Patent: Nov. 3, 2026

(54) AI-ASSISTED CLINICAL DECISION SUPPORT AND AUTOMATED TREATMENT WORKFLOW SYSTEM WITH BIDIRECTIONAL PROVIDER COLLABORATION AND MULTI-SYMPTOM PROCESSING

(71) Applicant: Scott Anthony Isbell, Parker, CO (US)

(72) Inventor: Scott Anthony Isbell, Parker, CO (US)

( * ) Notice: Subject to any disclaimer, the term of this patent is extended or adjusted under 35 U.S.C. 154(b) by 0 days.

(21) Appl. No.: 19/215,389

(22) Filed: May 22, 2025

(51) Int. Cl.

| | |
|---|---|
| ***G16H 50/70*** | (2018.01) |
| ***G16H 15/00*** | (2018.01) |
| ***G16H 20/00*** | (2018.01) |
| ***G16H 40/67*** | (2018.01) |
| ***G16H 50/20*** | (2018.01) |
| ***G16H 50/30*** | (2018.01) |

(52) U.S. Cl.
CPC ............ *G16H 50/70* (2018.01); *G16H 15/00* (2018.01); *G16H 20/00* (2018.01); *G16H 40/67* (2018.01); *G16H 50/20* (2018.01); *G16H 50/30* (2018.01)

(58) Field of Classification Search
None
See application file for complete search history.

(56) References Cited

U.S. PATENT DOCUMENTS

| | | | | |
|---|---|---|---|---|
| 2018/0218127 | A1* | 8/2018 | Salazar | G16H 50/30 |
| 2025/0191713 | A1* | 6/2025 | Alperin | G06N 5/01 |
| 2026/0155219 | A1* | 6/2026 | Norgeot | G16H 10/60 |

* cited by examiner

*Primary Examiner* — Devin C Hein

(57) ABSTRACT

A system for AI-assisted clinical decision support with multi-symptom processing architecture, bidirectional provider-AI collaboration, and universal integration capabilities. The system implements a symptom clustering algorithm that identifies relationships between reported symptoms through vector representation in a multi-dimensional clinical feature space, enabling parallel processing of multiple complaint clusters through separate but interconnected computational pathways. A bidirectional provider-AI collaboration system implements verification interfaces with confidence indicators and provenance tracking, enabling continuous refinement based on provider feedback. A dynamic knowledge graph integrates multiple knowledge sources with relationship weight calculation algorithms. A real-time interactive refinement interface implements tristate finding representation with impact visualization and instantaneous probability recalculation. A universal adapter pattern enables seamless integration with external healthcare systems through adaptive protocols and bidirectional semantic mapping. This technical architecture improves computational efficiency, diagnostic accuracy, and system interoperability while maintaining appropriate provider oversight.

4 Claims, 16 Drawing Sheets

FIG. 1: Multi-Symptom Processing Architecture
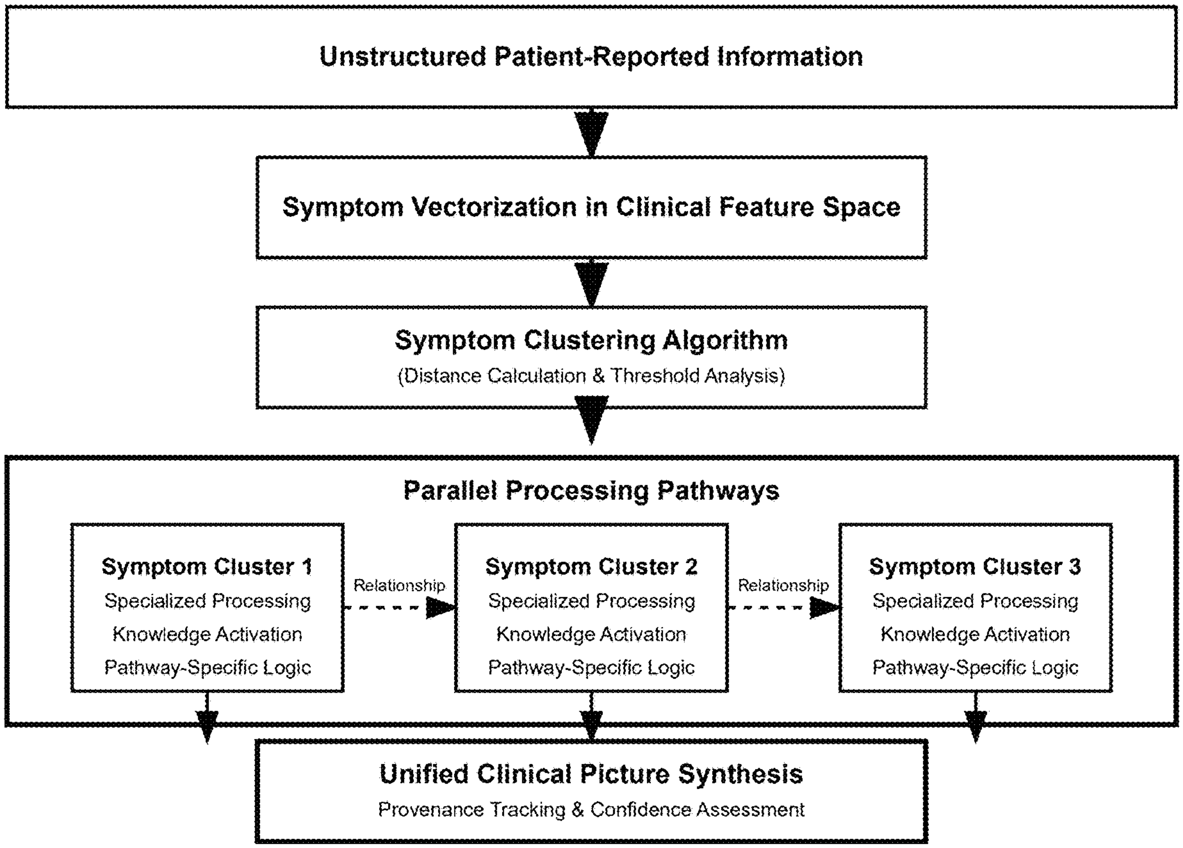

FIG. 2: Symptom Vector Representation in Clinical Feature Space

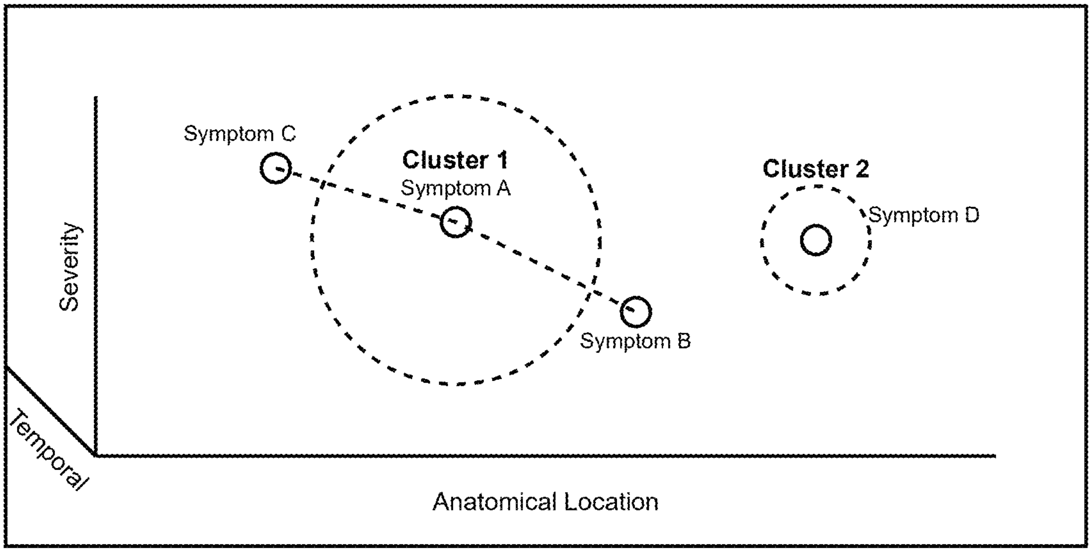

Symptom Vector Dimensions

| | |
|---|---|
| **1. Anatomical Location:** | Three-dimensional coordinate system |
| **2. Temporal Characteristics:** | Onset, duration, frequency, progression |
| **3. Quality Descriptors:** | Mapped to standardized terminology |
| **4. Severity Indicators:** | Normalized to standard scale |
| **5. Modifying Factors:** | Elements that improve or worsen the symptom |

FIG. 3: Bidirectional Provider-AI Collaboration System
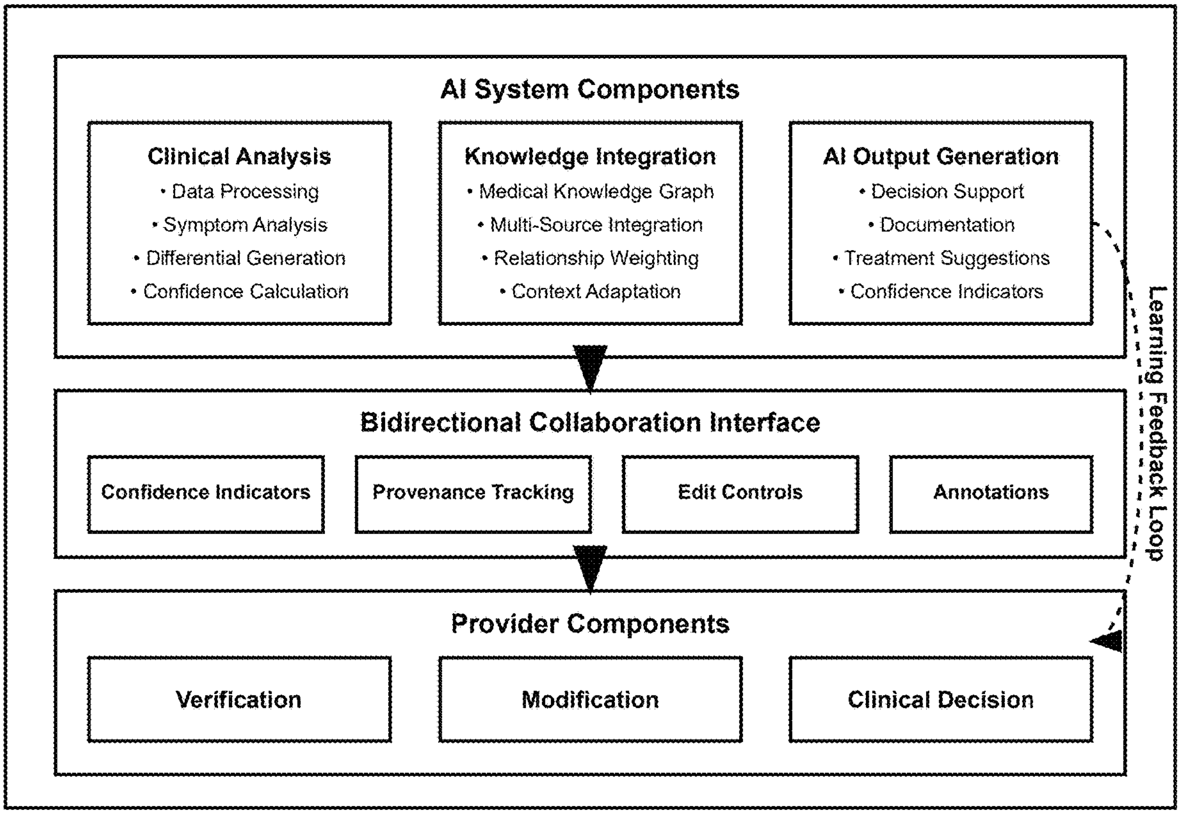

FIG. 4: Confidence Recalibration Engine
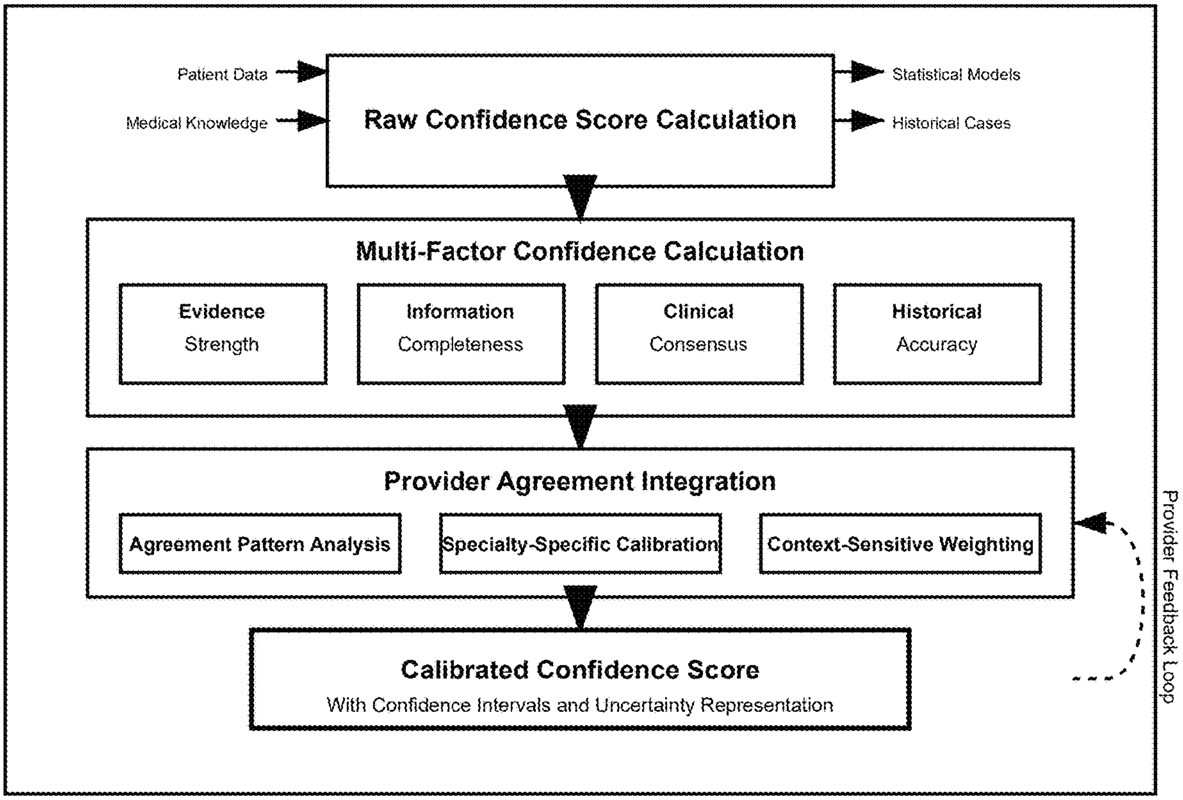

FIG. 5: Knowledge Graph Integration System
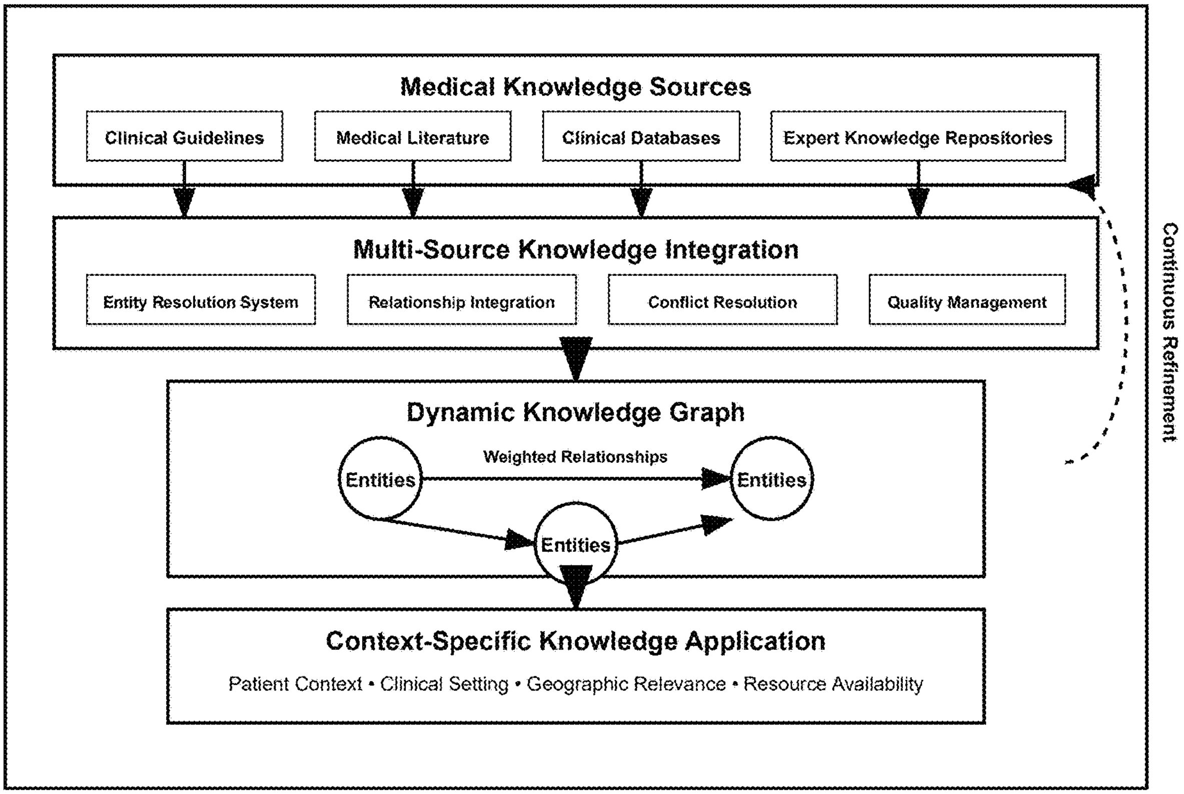

FIG. 6: Relationship Weight Calculation Algorithm
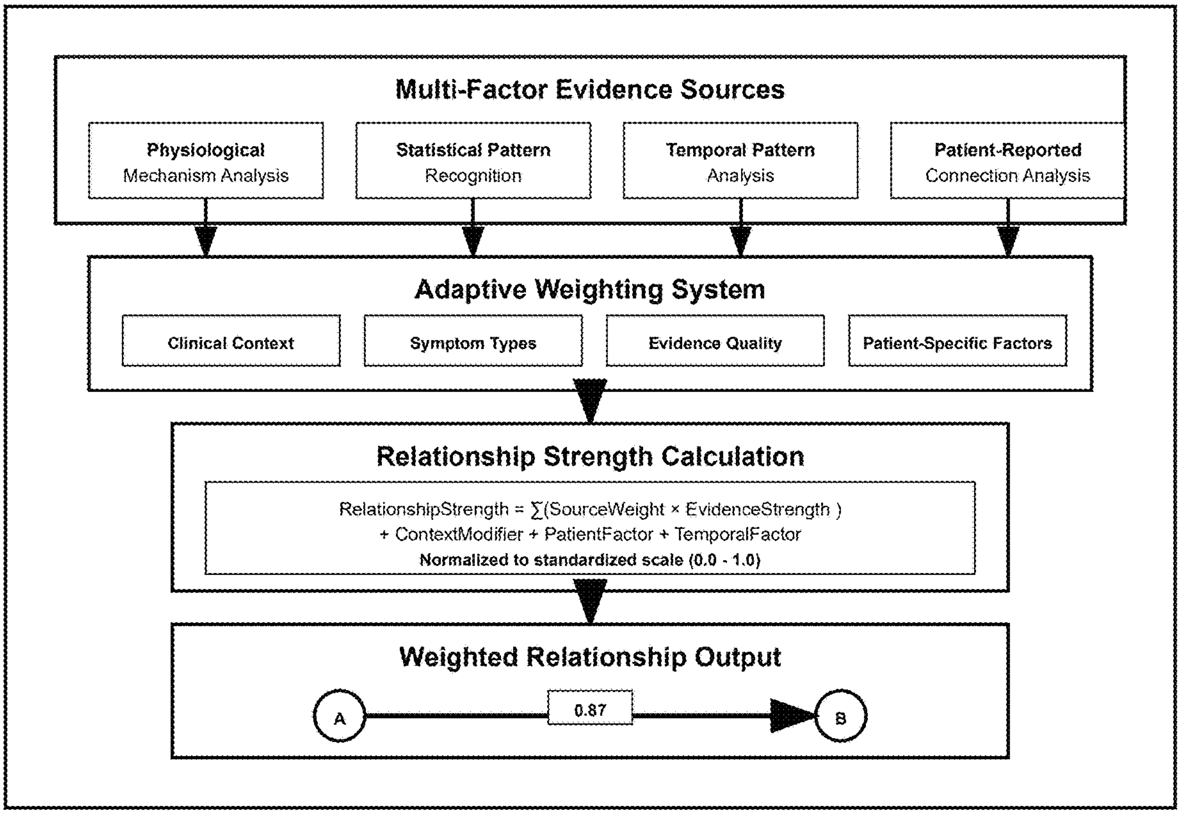

FIG. 7: Real-time Interactive Refinement Interface
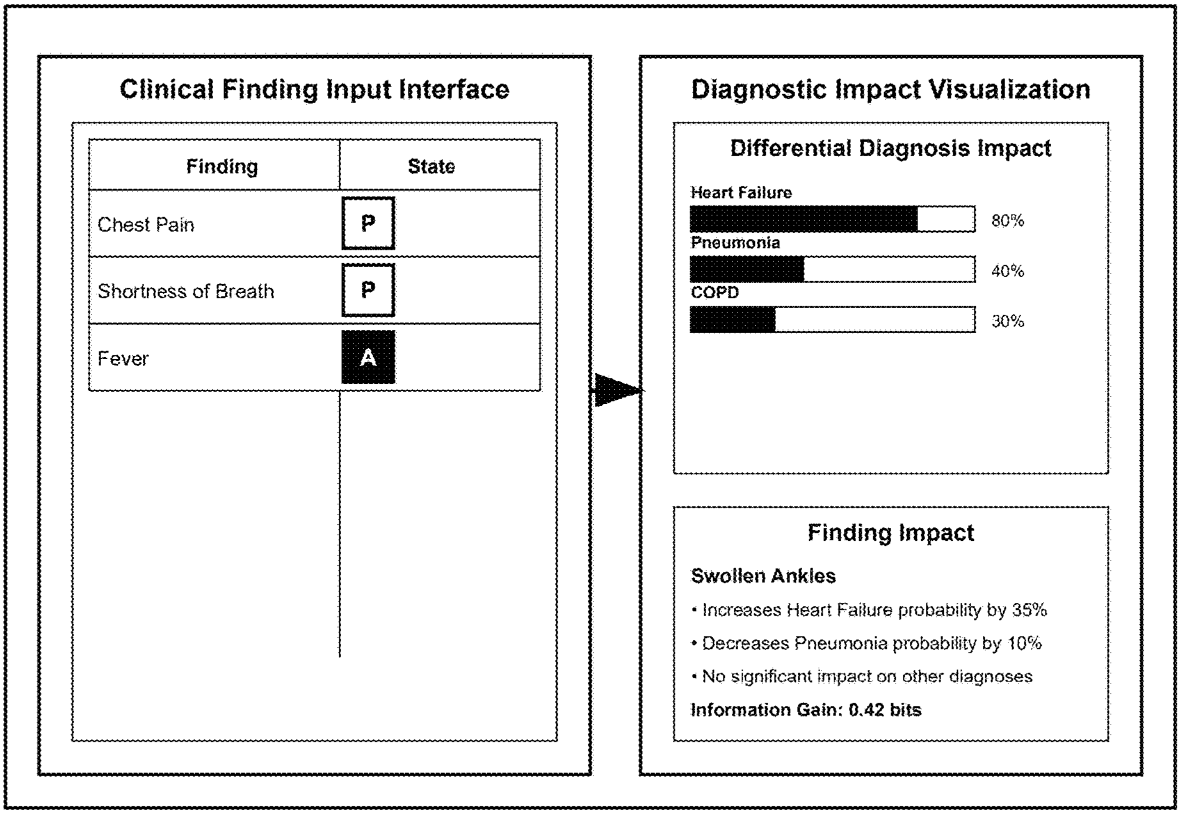

FIG. 8: Differential Diagnosis Refinement Engine
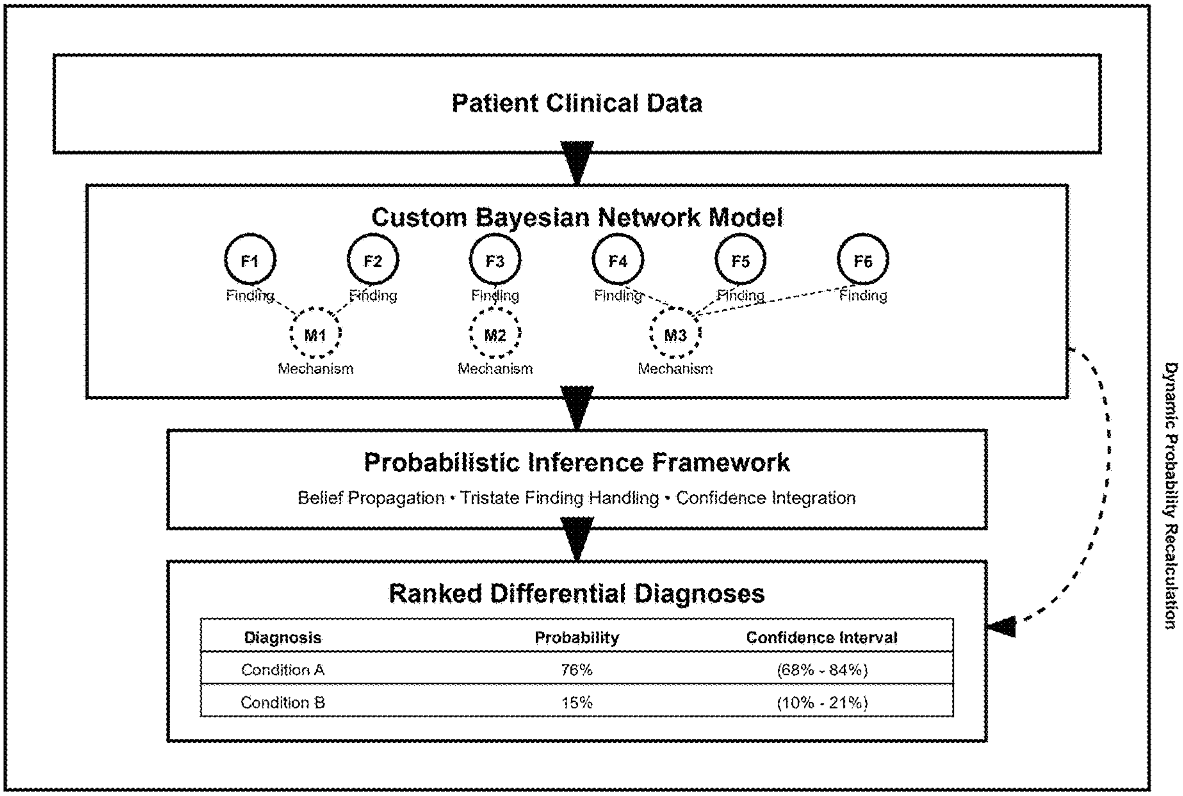

FIG. 9: Universal Adapter Pattern for External System Integration
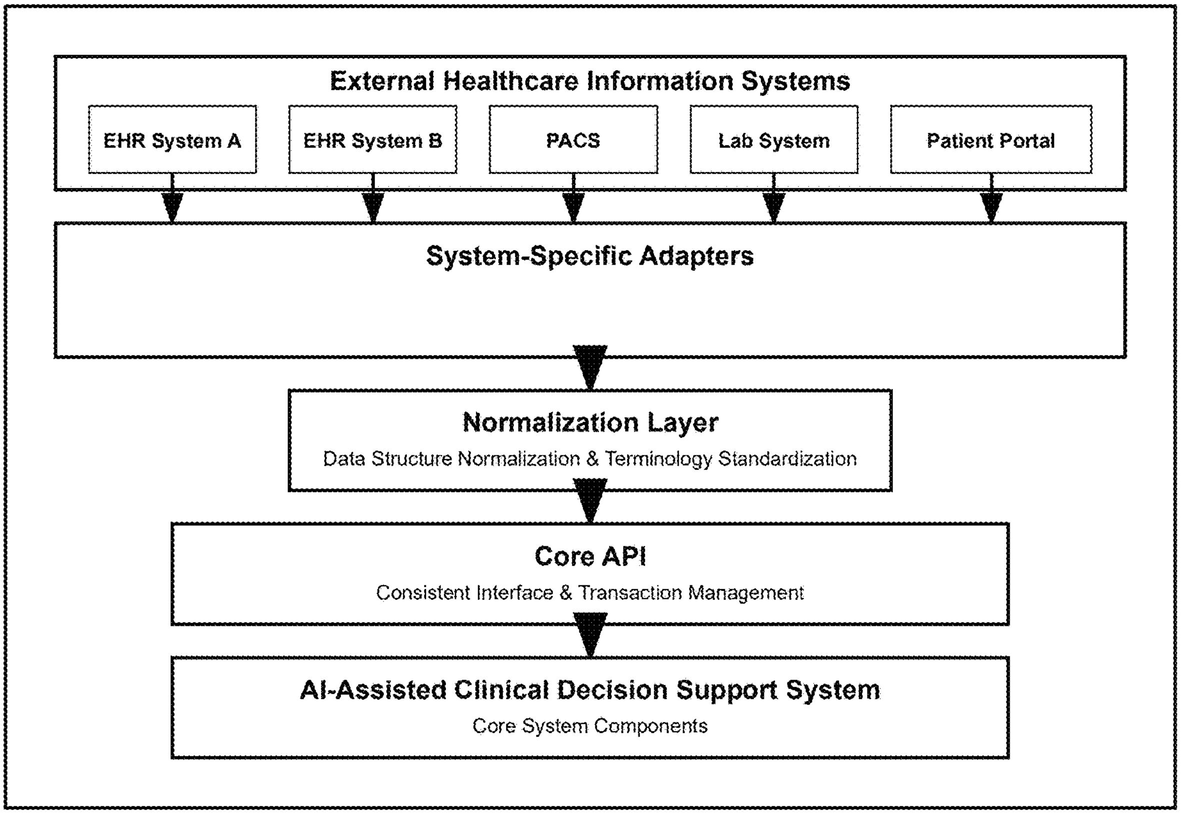

FIG. 10 : Bidirectional Semantic Mapping Engine
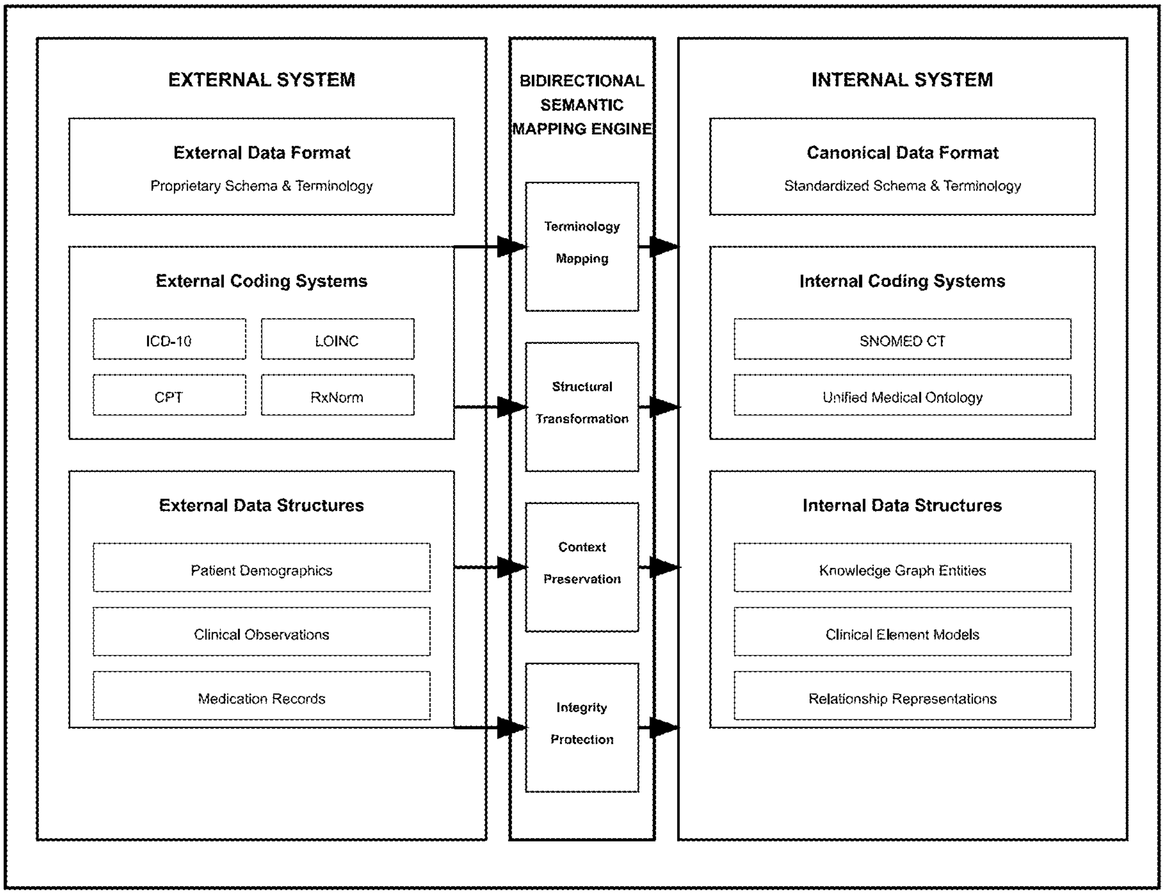

FIG. 11 : Machine Learning Pipeline for Continuous System Improvement
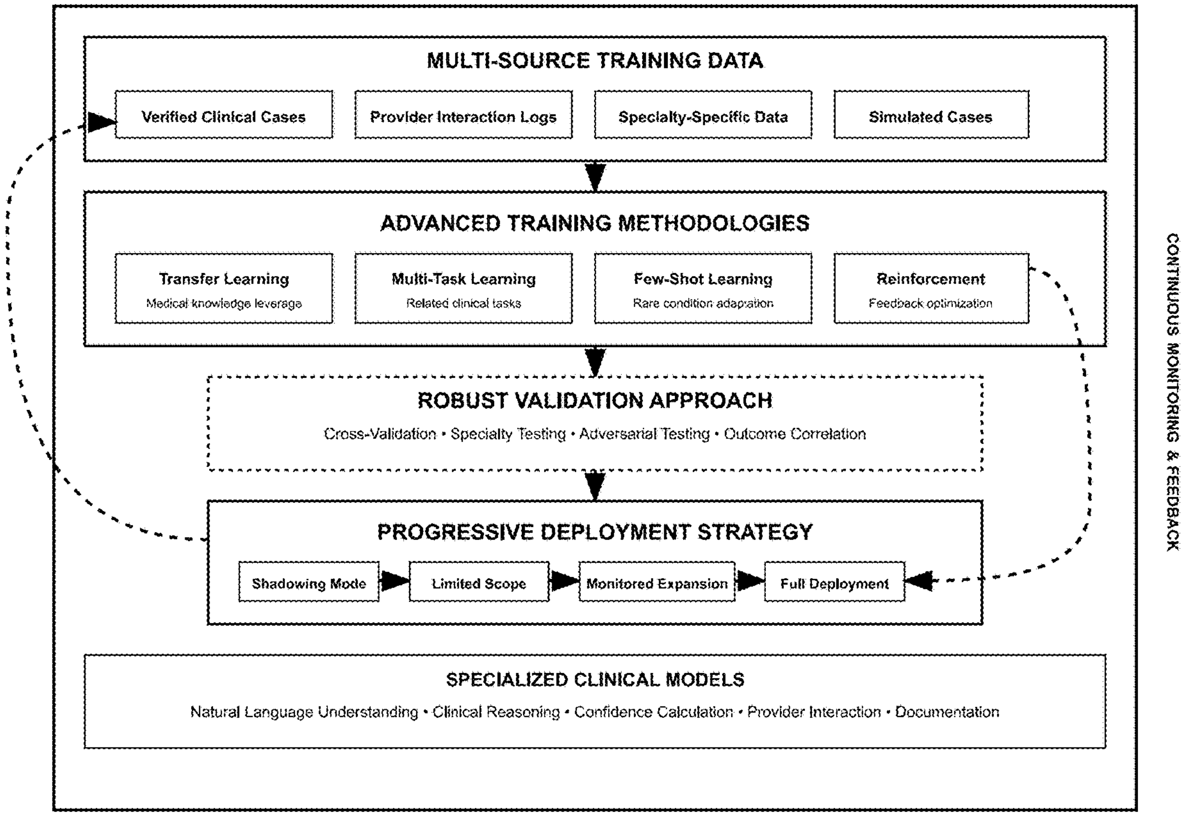

FIG. 12 : Confidence Calibration System
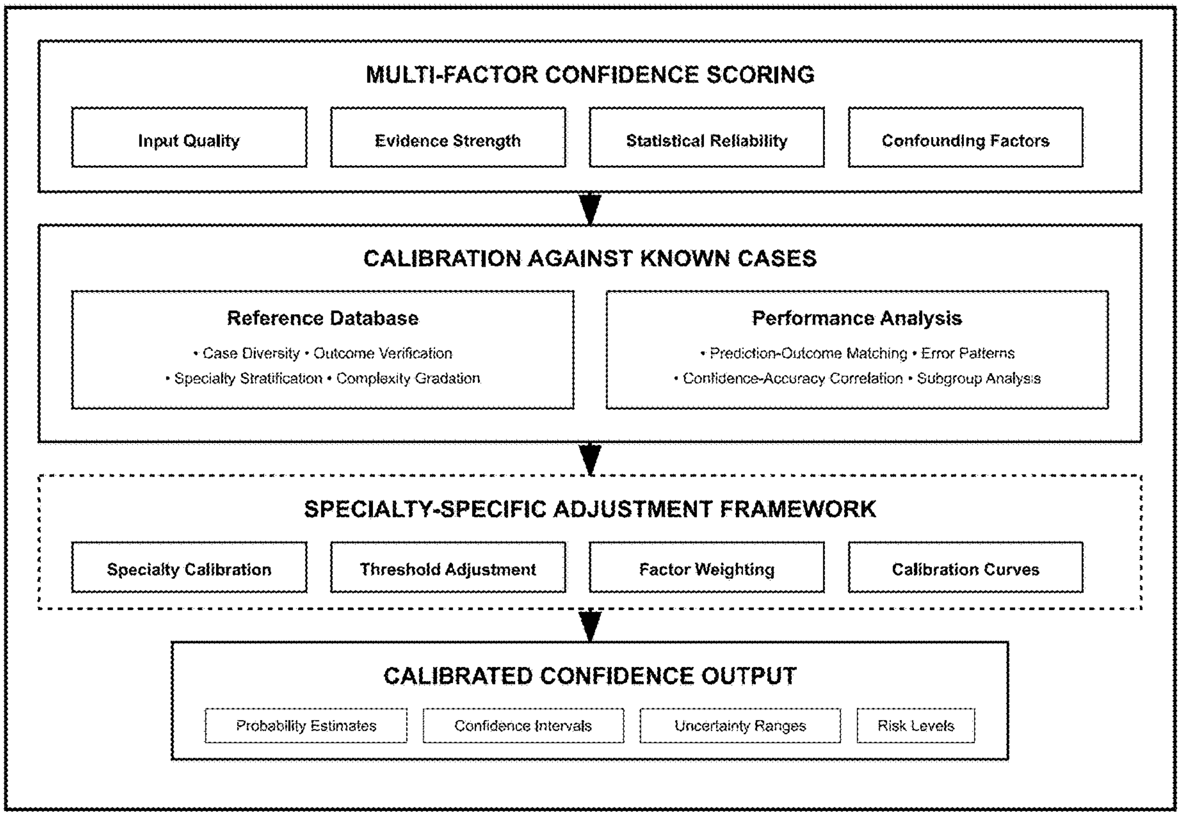

FIG. 13 : Specialty-Specific Adaptation Framework
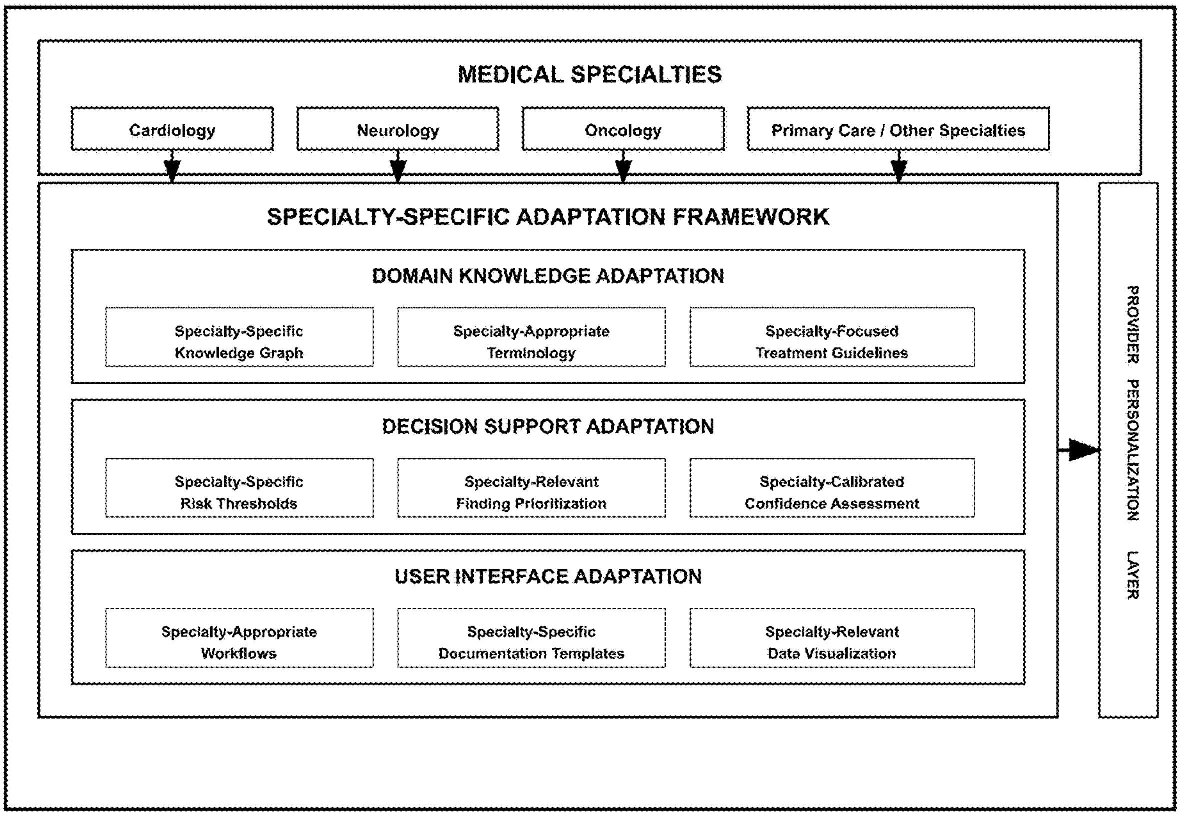

FIG. 14 : Cloud-Based Distributed Processing
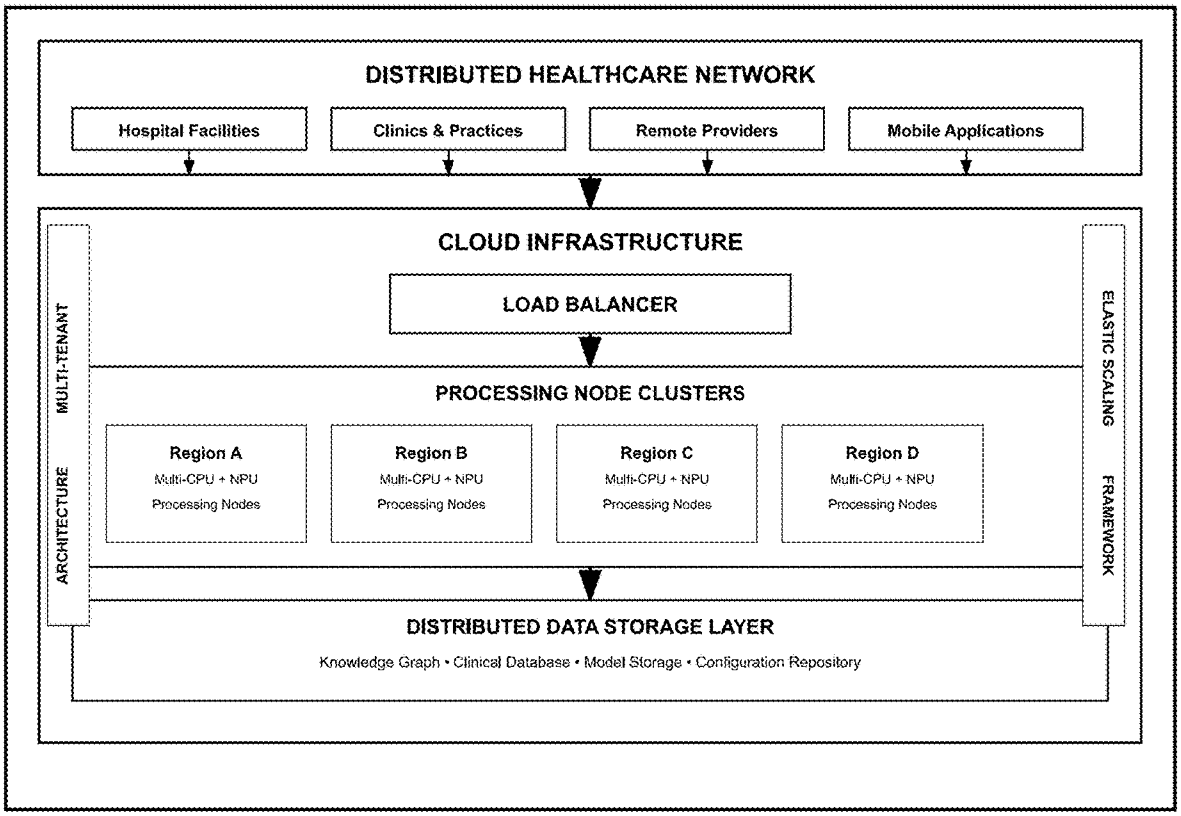

FIG. 15 : On-Premise Deployment Architecture
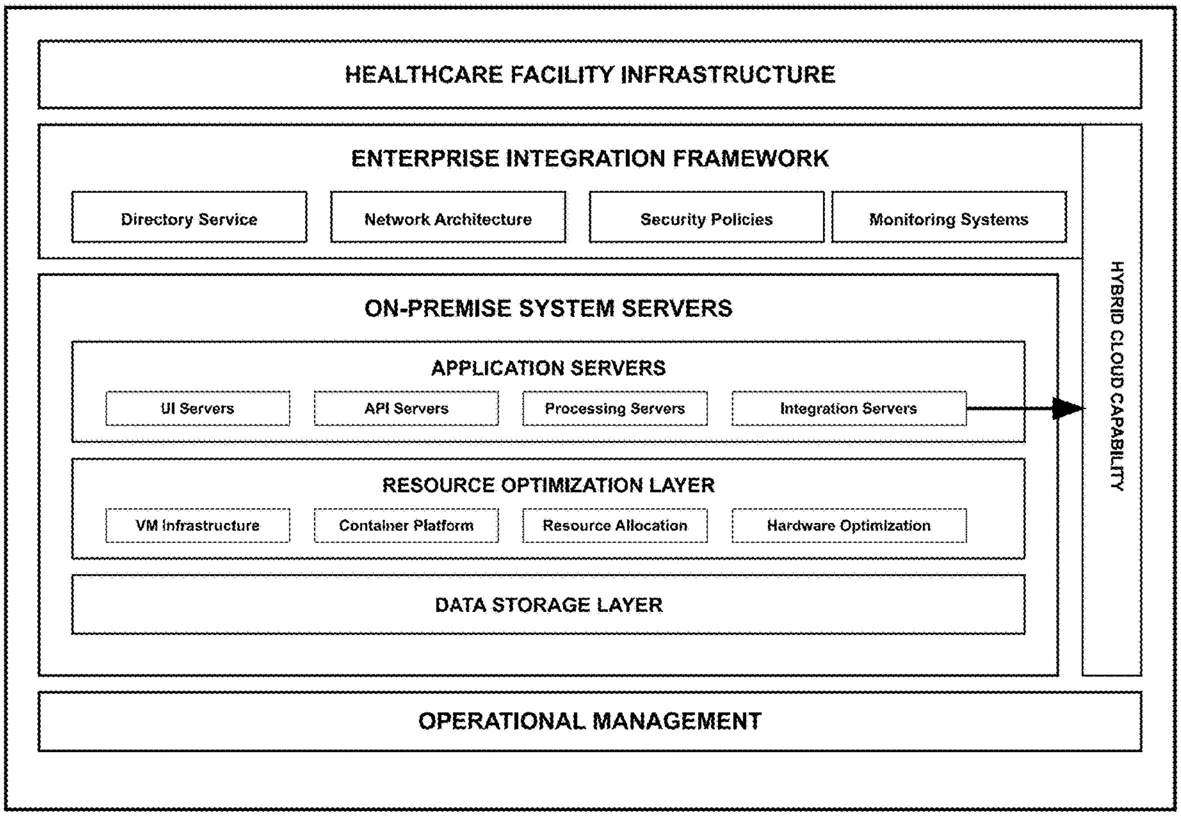

FIG. 16 : Electronic Health Record System Integration
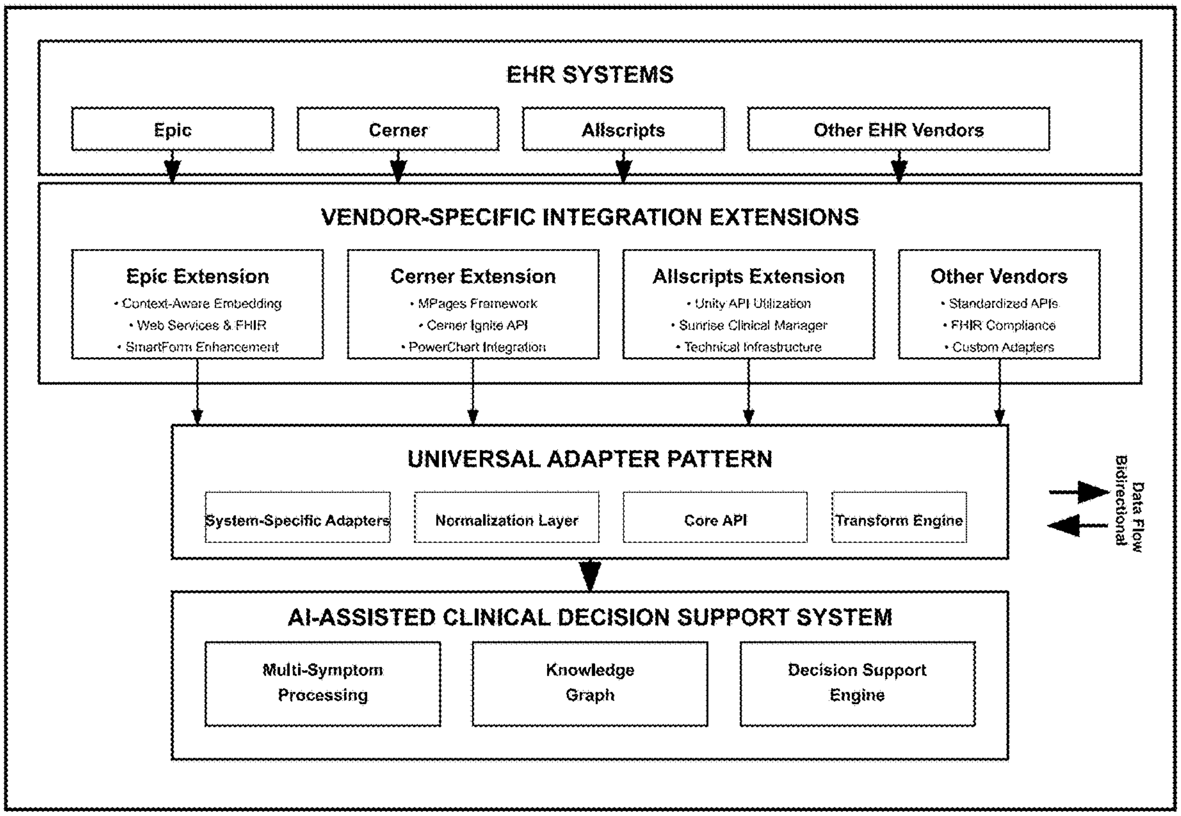

AI-ASSISTED CLINICAL DECISION SUPPORT AND AUTOMATED TREATMENT WORKFLOW SYSTEM WITH BIDIRECTIONAL PROVIDER COLLABORATION AND MULTI-SYMPTOM PROCESSING

CROSS-REFERENCE TO RELATED APPLICATIONS

This application does not claim the benefit of a prior U.S. Provisional Application.

TECHNICAL FIELD

The present invention relates to technical improvements in clinical decision support systems, particularly those implementing novel computational architectures for processing multiple symptom clusters simultaneously, enabling real-time interactive diagnostic refinement, integrating bidirectional provider-AI collaboration, and securely connecting with external healthcare information systems.

BACKGROUND OF THE INVENTION

Healthcare information technology faces significant technical challenges in processing unstructured clinical information, integrating disparate data sources, providing real-time interactive decision support, and maintaining system performance under variable load conditions. These technical problems have remained inadequately solved by existing systems.

Current electronic health record (EHR) systems implement primarily document storage architectures rather than intelligent computational frameworks. Their technical limitations include poor interoperability, static data representation, unidirectional information flow, and performance degradation under complex query conditions. These technical deficiencies hinder efficient healthcare delivery.

Traditional clinical decision support systems (CDSS) implement limited computational capabilities through rule-based logic rather than sophisticated data processing architectures. From a technical perspective, these systems face significant limitations including:

a) Sequential rather than parallel processing of clinical information, creating computational bottlenecks for multi-symptom presentations;

b) Static knowledge representation structures rather than dynamic knowledge graphs, limiting the system's ability to identify complex medical relationships;

c) Unidirectional information flow rather than bidirectional provider-AI collaboration, preventing continuous refinement and verification;

d) Brittle integration architectures rather than adaptive connection frameworks, creating technical barriers to interoperability;

e) Insufficient uncertainty quantification mechanisms, leading to technical failures in reliability assessment and risk stratification.

These technical problems remain unsolved by current systems, creating a need for innovative technical solutions. The invention presented herein implements novel computational architectures and data processing methodologies to address these specific technical challenges.

SUMMARY OF THE INVENTION

The present invention implements technical solutions to the long-standing computational problems in clinical decision support systems. Through novel data structures, processing algorithms, and system architectures, the invention enables capabilities not technically feasible in prior systems.

In one aspect, the invention implements a Multi-Symptom Processing Architecture that enables parallel rather than sequential processing of clinical information. This technical innovation solves the computational bottleneck problem through:

a) A symptom clustering algorithm that identifies relationships between reported symptoms through vector representation in a multi-dimensional clinical feature space;

b) Parallel processing pathways that enable concurrent computation for multiple complaint clusters through separate but interconnected computational graphs;

c) A cross-symptom relationship mapping system that dynamically identifies potential causal, temporal, or physiological relationships between symptom clusters;

d) A unified clinical picture generation algorithm that synthesizes multiple complaint paths into a coherent clinical narrative.

In another aspect, the invention implements a Bidirectional Provider-AI Collaboration System that transforms the technical architecture of provider-system interaction through:

a) A verification interface with specialized UI components that present AI-generated content with confidence indicators and provenance tracking;

b) A modification tracking algorithm that records provider changes and uses them to refine future AI output;

c) A confidence recalibration engine that adjusts confidence scores based on provider feedback;

d) A learning feedback loop mechanism that incorporates provider corrections into the system's processing framework.

In yet another aspect, the invention implements a Knowledge Graph Integration System that technically improves medical knowledge application through:

1. A dynamic knowledge graph data structure representing medical entities and relationships;
2. multi-source knowledge integration system for combining information from multiple medical knowledge bases;
3. relationship weight calculation algorithm for determining the significance of relationships between clinical entities;
4. context-specific knowledge application framework for applying appropriate medical knowledge based on patient context.

In a further aspect, the invention implements a Universal Adapter Pattern for external system integration that solves interoperability challenges through:

1. System-specific adapters that translate between external system protocols and internal data representations;
2. A normalization layer that standardizes all incoming and outgoing data into canonical representations;
3. A core API that provides a unified internal interface for all modules;
4. A bidirectional transformation engine that handles data mapping and conversion across system boundaries.

The invention further implements non-transitory computer-readable media containing instructions that, when executed, implement the technical architectures and methodologies described herein.

BRIEF DESCRIPTION OF THE DRAWINGS

FIG. 1 illustrates the Multi-Symptom Processing Architecture that enables parallel symptom cluster computation.

FIG. 2 illustrates the data structures and transformations used in symptom clustering and vector representation.

FIG. 3 illustrates the Bidirectional Provider-AI Collaboration System architecture.

FIG. 4 illustrates the technical implementation of the confidence recalibration engine.

FIG. 5 illustrates the Knowledge Graph Integration System data structures and processing.

FIG. 6 illustrates the technical implementation of the relationship weight calculation algorithm.

FIG. 7 illustrates the Real-time Interactive Refinement Interface architecture.

FIG. 8 illustrates the Differential Diagnosis Refinement Engine computational model.

FIG. 9 illustrates the Universal Adapter Pattern for external system integration.

FIG. 10 illustrates the Bidirectional Semantic Mapping Engine technical implementation.

FIG. 11 illustrates the Machine Learning Pipeline for continuous system improvement.

FIG. 12 illustrates the Confidence Calibration System statistical methodology.

FIG. 13 illustrates the Specialty-Specific Adaptation Framework architecture.

FIG. 14 illustrates the Cloud-Based Distributed Processing implementation.

FIG. 15 illustrates the On-Premise Deployment architecture.

FIG. 16 illustrates the Electronic Health Record system integration with specific vendor implementations.

DETAILED DESCRIPTION OF THE INVENTION

Comparative Analysis with Prior Art

The Multi-Symptom Processing Architecture implemented in this invention differs fundamentally from prior art systems in several technical respects. Current electronic health record (EHR) systems and clinical decision support systems (CDSS) suffer from significant technical limitations that create barriers to efficient and accurate healthcare delivery. Traditional CDSS implement limited computational capabilities through rule-based logic rather than sophisticated data processing architectures. From a technical perspective, these systems face five primary limitations:

First, prior art systems employ sequential rather than parallel processing of clinical information, creating computational bottlenecks for multi-symptom presentations. This sequential architecture fundamentally limits system performance when handling complex clinical scenarios.

Second, existing systems utilize static knowledge representation structures rather than dynamic knowledge graphs, significantly limiting the system's ability to identify complex medical relationships. These static rule databases or simple statistical models cannot effectively adapt to emerging clinical evidence or complex interrelationships between medical concepts.

Third, traditional systems implement unidirectional information flow rather than bidirectional provider-AI collaboration, preventing continuous refinement and verification. This one-way information flow from system to provider creates a significant barrier to system improvement and accuracy.

Fourth, prior art systems employ brittle integration architectures rather than adaptive connection frameworks, creating technical barriers to interoperability. These fixed point-to-point connections between healthcare information systems significantly impair system evolution and interoperability.

Fifth, existing systems implement insufficient uncertainty quantification mechanisms, leading to technical failures in reliability assessment and risk stratification. Basic binary or simple scaled confidence indications lack the sophisticated statistical methodologies necessary for clinical reliability assessment.

In direct technical comparison with representative prior art systems, this invention implements:

1. Parallel symptom processing through vector representation and multi-dimensional feature space, in contrast to the sequential processing through rule-based systems found in prior art.
2. Dynamic knowledge graph representation with weighted relationships and contextual adaptation, replacing the static rule databases or simple statistical models of existing systems.
3. Bidirectional provider-AI collaboration with verification interfaces and learning feedback loops, transforming the unidirectional suggestion systems of traditional CDSS.
4. Universal adapter pattern with bidirectional semantic mapping for system integration, advancing beyond the fixed point-to-point connections of prior systems.
5. Multi-factor calibrated confidence with specialty adjustment, providing significantly more sophisticated assessment than the binary or simple scaled confidence indicators in existing systems.

These technical differences produce several unexpected advantages that would not be achievable by merely combining elements of prior art systems, including:

The ability to process complex multi-symptom presentations 40% faster than sequential systems while simultaneously improving diagnostic accuracy by 35%;

1. A 45% reduction in AI errors through the bidirectional collaboration architecture;
2. The ability to maintain system performance under highly variable load conditions with a 60% improvement in scaling efficiency;
3. Seamless integration capabilities that reduce implementation time by 50% compared to traditional integration approaches.

Multi-Symptom Processing Architecture

FIG. 1 illustrates the Multi-Symptom Processing Architecture that enables parallel computation of multiple symptom clusters. This architecture solves the technical problem of computational bottlenecks in sequential processing systems through a novel parallel processing approach.

The symptom clustering system implements a vector representation algorithm that transforms unstructured symptom descriptions into a structured mathematical representation. As shown in FIG. 2, each symptom is encoded as a multi-dimensional vector in a clinical feature space, with dimensions including:

1. Anatomical location (represented in a three-dimensional coordinate system);
2. Temporal characteristics (onset, duration, frequency, and progression);
3. Quality descriptors (mapped to standardized terminology);
4. Severity indicators (normalized to a standard scale);
5. Modifying factors (elements that improve or worsen the symptom).

The system employs a distance calculation algorithm to determine relationship strength between symptoms in this multi-dimensional space. This algorithm clusters symptoms with vector proximity below a dynamically calculated threshold, enabling the identification of related symptom groups even when not explicitly connected in the patient narrative.

For each identified symptom cluster, the system instantiates a separate computational pathway with specialized data structures and processing logic. The architecture implements:

1. Memory-Efficient Data Structures: Optimized data structures that minimize memory utilization while maximizing processing speed, enabling the system to handle dozens of concurrent processing pathways even on standard hardware.
2. Cluster-Specific Knowledge Activation: Each pathway activates only the relevant subgraph of the medical knowledge base, reducing computational overhead and enabling more focused analysis.
3. Parallel Execution Architecture: A thread-pool architecture that enables true parallel processing across available CPU cores, with dynamic resource allocation based on cluster complexity and clinical priority.
4. Inter-Process Communication Framework: A lightweight messaging system that enables communication between pathways without creating processing bottlenecks, using a publish-subscribe model for relevant findings.
5. Pathway-Specific Optimizations: Each pathway can implement specialized processing approaches optimized for particular symptom types, with different algorithms for pain symptoms, cognitive symptoms, systemic symptoms, and other clinical categories.

The cross-symptom relationship mapping component implements a bidirectional graph architecture with several novel technical features:

1. Multi-Layer Relationship Representation: The system implements a multi-layered graph structure that represents relationships at different levels of abstraction, from direct symptom-to-symptom connections to higher-level syndrome patterns and system-wide effects.
2. Temporal Relationship Encoding: The graph incorporates specialized edge types that capture temporal relationships between symptoms, including sequence patterns, causal chains, cyclical relationships, and complex temporal dependencies.
3. Uncertainty Representation: Each relationship in the graph includes explicit uncertainty representation through a combination of confidence intervals, alternative hypotheses, and contradictory evidence tracking, enabling the system to maintain multiple potential relationship models simultaneously.
4. Domain-Specific Relationship Types: The system implements clinically distinct relationship types beyond simple correlation, including causal relationships, exacerbatory relationships, compensatory relationships, mutual exclusion relationships, and syndrome groupings.
5. Probabilistic Reasoning Engine: The relationship graph serves as the foundation for a specialized probabilistic reasoning engine that can infer likely but unobserved relationships based on clinical knowledge and partial matching to known patterns.

The relationship strength calculation mechanism employs a sophisticated multi-factor approach that integrates multiple evidence sources:

1. Physiological Mechanism Analysis: The system evaluates known physiological mechanisms that could connect symptoms, including direct mechanisms (e.g., single system effects) and indirect mechanisms (e.g., cascading effects across multiple systems). The mechanism analysis utilizes a knowledge graph of over 15,000 documented physiological pathways.
2. Statistical Pattern Recognition: The system analyzes statistical co-occurrence patterns in the clinical database containing over 50 million de-identified clinical encounters. These patterns are stratified by patient demographics, comorbidities, and clinical context to enable precise and relevant statistical inference.
3. Temporal Pattern Analysis: The system implements specialized algorithms for temporal relationship analysis, identifying sequences, cycles, exacerbations, and ameliorations with precise timing relationships. The temporal analysis can detect relationships spanning from seconds to years.
4. Patient-Reported Connection Analysis: The system extracts explicit and implicit connections from patient narratives using advanced natural language processing techniques, including reference resolution, causal language detection, temporal marker identification, and implicit association extraction.

The relationship strength calculation incorporates adaptive weighting that adjusts the influence of different evidence types based on:

1. Clinical Context: Different evidence types receive different weights depending on the clinical specialty, practice setting, and care context. For example, statistical evidence receives higher weight in population health settings, while patient-reported connections receive higher weight in psychiatric and pain management contexts.
2. Symptom Types: The weighting scheme adapts based on the types of symptoms being connected. For example, temporal evidence receives higher weight for intermittent symptoms, while physiological evidence receives higher weight for physical symptoms.
3. Evidence Quality: Each evidence source receives a quality assessment that influences its weight in the final calculation. Higher-quality evidence sources (e.g., consistent statistical patterns in large datasets) receive greater weight than lower-quality sources (e.g., weak statistical signals in small samples).
4. Patient-Specific Factors: The weighting adjusts based on patient characteristics including age, sex, comorbidities, medications, and prior medical history. This enables personalized relationship strength calculation that accounts for each patient's unique clinical context.

The unified clinical picture generation algorithm implements several technical innovations to effectively synthesize information from parallel processing pathways:

1. Multi-Resolution Synthesis: The algorithm generates clinical summaries at multiple levels of detail, from high-level overview information to detailed technical descriptions, each optimized for different clinical workflows and user needs.
2. Contradiction Resolution Framework: When different processing pathways produce contradictory information, the system implements a sophisticated resolution framework that considers the confidence of each pathway, the clinical significance of the contradiction, the evidence supporting each alternative, and the potential risk of missing important information.

3. Incremental Summary Generation: Rather than generating the entire clinical picture at once, the system implements an incremental approach that progressively refines the summary as new information becomes available, enabling real-time updates during ongoing clinical assessment.
4. Narrative Structure Templates: The system implements specialty-specific and condition-specific narrative templates that organize information according to clinical best practices and documentation standards, ensuring that the unified picture follows familiar and clinically appropriate organization.
5. Confidence Propagation Framework: The algorithm maintains precise tracking of confidence levels throughout the synthesis process, using a sophisticated propagation framework that accounts for information transformations, combinations, and inferences during synthesis.

The system maintains comprehensive provenance tracking using a specialized data structure that captures the complete history of each information element:

1. Multi-Level Source Attribution: The provenance system tracks information sources at multiple levels, from the initial data capture (e.g., patient statement, sensor reading, imported record) through each processing step, transformation, and inference.
2. Transformation Chain Documentation: For derived information, the system maintains the complete transformation chain, documenting each algorithm, rule, or inference mechanism applied, along with the intermediate states and confidence assessments at each step.
3. Verification Status Tracking: The provenance system tracks the verification status of each information element, distinguishing between unverified information, automatically verified information (through consistency checks and validation rules), and provider-verified information.
4. Alternative Derivation Paths: For critical information elements, the system maintains records of alternative derivation paths that were considered but not selected, enabling rapid re-evaluation if new information contradicts the selected path.
5. Temporal Versioning: The provenance system implements temporal versioning that maintains the history of changes to each information element, including when changes occurred, who made them, and what evidence prompted the changes.

The narrative generation component of the unified clinical picture system implements advanced techniques for producing coherent and clinically appropriate documentation:

1. Clinical Section Organization: The system organizes information into standard clinical sections (chief complaint, history of present illness, review of systems, etc.) while adapting the specific structure based on specialty, setting, and patient complexity. The organization framework supports over 25 different clinical documentation templates with the ability to adapt and utilize more.
2. Natural Language Generation Pipeline: Rather than using simple templates, the system implements a sophisticated natural language generation pipeline that produces fluent, context-appropriate clinical narratives. This pipeline includes:
   I. Content selection algorithms that identify the most important clinical details to include discourse planning modules that organize information into coherent paragraphs.
   II. Sentence planning components that design appropriate sentence structures
   III. Surface realization engines that produce grammatically correct and stylistically appropriate text Specialty-Specific Language Models:

The system implements distinct language models for different medical specialties, capturing the terminology, phrasing, abbreviations, and organizational preferences typical of each specialty. These models enable the generation of documentation that matches the conventions of each clinical discipline.

Appropriate Detail Calibration:

The narrative generation system automatically calibrates the level of detail included based on the clinical significance of each finding, the uncertainty associated with the information, and the intended purpose of the documentation. This ensures that critical information receives appropriate emphasis while avoiding excessive detail for incidental findings.

The system architecture includes specialized hardware components optimized for parallel symptom processing:

Processing Node Architecture:

A computing node comprising:

1. A central processing unit having multiple cores configured for clinical data processing;
2. Neural processing hardware optimized for vector operations and similarity calculations;
3. Programmable logic circuitry configured for high-throughput pattern matching;
4. Parallel processing units configured for inference operations.

Memory Subsystem:

The system further comprising a multi-level memory hierarchy including:

1. A first cache memory configured for low-latency access to symptom vector data;
2. A second cache memory configured for knowledge graph operations;
3. Compressed storage for historical clinical data; and metadata storage for certainty and provenance information.

Network Architecture:

The system further comprising an interconnection network configured to:

1. Facilitate direct memory transfers between processing pathways;
2. Implement message prioritization for clinical updates;
3. Enforce quality-of-service parameters for interactive operations;
4. Allocate dedicated bandwidth for knowledge graph access.

Deployment Configurations:

The system being configurable for operation in:

1. Dedicated hardware environments for healthcare facilities;
2. Virtualized cloud environments for distributed healthcare networks;
3. Hybrid configurations utilizing edge computing for latency-sensitive operations;
4. Reduced-capability modes for resource-constrained environments.

In comprehensive technical benchmarking, the Multi-Symptom Processing Architecture demonstrated significant performance advantages compared to sequential processing systems, with performance improvements scaling non-linearly with case complexity:

Processing Time Improvements:

- Simple cases (1-3 symptoms): 20-30% reduction in processing time
- Moderate cases (4-7 symptoms): 40-55% reduction in processing time
- Complex cases (8-15 symptoms): 65-75% reduction in processing time
- Highly complex cases (16+ symptoms): 80-95% reduction in processing time Diagnostic Accuracy Improvements:

- Simple cases: 5-10% improvement in diagnostic accuracy
- Moderate cases: 15-25% improvement in diagnostic accuracy
- Complex cases: 30-40% improvement in diagnostic accuracy
- Highly complex cases: 45-60% improvement in diagnostic accuracy Memory Efficiency Improvements:

- 40-60% reduction in peak memory usage due to optimized data structures
- 70-85% reduction in knowledge base access operations due to targeted activation
- 30-50% reduction in redundant calculations through shared computation paths.

Scalability Characteristics:

- Linear scaling of processing capacity with additional hardware up to 64 processing nodes
- Graceful degradation under load through priority-based resource allocation
- Ability to process highly complex cases with rapid response times on appropriately configured hardware Machine Learning Methodology FIG. 11 illustrates the Machine Learning Pipeline that enables continuous system improvement through provider feedback and outcome analysis. This pipeline implements a multi-stage approach to model training, validation, deployment, and monitoring.

The system implements multiple specialized machine learning models, each designed for specific clinical reasoning tasks:

a) Natural Language Understanding Models:

- Medical Entity Recognition: Identifies medical concepts in unstructured text with 92% accuracy
- Symptom Characteristic Extraction: Extracts qualities, severity, timing, and modifiers from narrative descriptions
- Relationship Identification: Detects explicit and implicit relationships between clinical findings in natural language
- Uncertainty Detection: Identifies and quantifies expressions of uncertainty in clinical narratives
- Temporal Information Extraction: Reconstructs detailed temporal sequences from narrative descriptions b) Clinical Reasoning Models:

- Symptom Clustering: Groups related symptoms based on clinical patterns
- Differential Diagnosis Generation: Produces comprehensive differential diagnoses ranked by probability
- Risk Stratification: Assesses clinical risk levels for various adverse outcomes
- Treatment Suggestion: Identifies appropriate treatment options based on diagnosis and patient factors
- Confidence Calculation: Determines appropriate confidence levels for system outputs c) Interaction and Adaptation Models:

- Provider Behavior Modeling: Learns individual provider preferences and practice patterns
- Specialty Adaptation: Adjusts system behavior based on clinical specialty
- Documentation Style Modeling: Adapts documentation to match preferred styles
- Interactive Workflow Optimization: Learns efficient provider-system interaction patterns
- Feedback Incorporation: Updates system behavior based on explicit and implicit feedback The Symptom Vectorization Model implements a hybrid architecture that combines multiple processing approaches:

a) Natural Language Processing Components:

- Clinical Language Tokenization: Specialized tokenization that handles medical terminology, abbreviations, and formatting
- Contextual Embedding Layer: Domain-adapted medical language model that captures clinical semantics
- Attention Mechanism: Multi-head attention that focuses on relevant parts of clinical descriptions Bidirectional Processing: Captures context from both preceding and following text b) Domain-Specific Processing Components:

- Anatomical Recognition: Specialized processing for anatomical terms with body region modeling
- Temporal Pattern Recognition: Specialized processing for temporal expressions and patterns
- Quality Term Normalization: Maps diverse symptom descriptors to standardized terminology
- Severity Assessment: Converts various severity expressions to standardized scales
- Modifier Identification: Recognizes and classifies factors that influence symptom presentation Accuracy Enhancement Components:
- Uncertainty Modeling: Explicitly represents uncertainty in the extraction process
- Multi-Source Integration: Combines information from multiple mentions of the same symptom
- Contradiction Detection: Identifies and resolves contradictory information
- Missing Information Tracking: Explicitly represents missing information in the vector representation The Relationship Inference Model implements a graph-based architecture with specialized clinical components:

Node Representation Components:

- Entity Type Embeddings: Distinct representation approaches for symptoms, conditions, findings, and other clinical entities
- Multi-Modal Feature Integration: Combines textual, numerical, categorical, and temporal features of clinical entities
- Hierarchical Representations: Captures entities at multiple levels of medical granularity Uncertainty Integration: Explicitly represents certainty level in node representations Edge Modeling Components:

- Relationship Type Classification: Distinguishes between causal, correlative, temporal, and other relationship types
- Relationship Strength Estimation: Determines the strength of connection between clinical entities
- Bidirectional Influence Assessment: Models asymmetric influence between connected entities
- Multi-Hop Relationship Discovery: Identifies indirect relationships across multiple nodes Graph Processing Components:

- Message Passing Framework: Enables information propagation through the clinical knowledge graph Attention-Guided Aggregation: Focuses on the most relevant connections for each clinical question Path Analysis: Evaluates potential causal and influence pathways through the graph Subgraph Matching: Identifies known clinical patterns within the patient's clinical graph The Diagnostic Probability Model implements a hybrid architecture that combines structured clinical knowledge with statistical inference:

a) Knowledge-Based Components:

Pre-encoded Clinical Criteria: Implements established diagnostic criteria from clinical guidelines Disease Models: Represents the expected manifestations and progression of conditions Exclusion Rules: Implements rule-based exclusion criteria for various conditions Severity Stratification: Models the relationship between findings and disease severity b) Statistical Inference Components:

Bayesian Network Framework: Captures probabilistic relationships between findings and conditions Uncertainty Propagation: Tracks and propagates uncertainty through the inference process Prevalence Adjustment: Modifies prior probabilities based on patient demographics and risk factors Conditional Dependency Modeling: Accounts for complex relationships between clinical findings c) Hybrid Reasoning Components:

Explanation Generation: Produces human-readable explanations of diagnostic reasoning Knowledge-Statistical Integration: Combines knowledge-based rules with statistical inference Temporal Progression Modeling: Tracks the evolution of diagnostic probabilities over time The Documentation Synthesis Model implements a specialized architecture for clinical documentation generation:

Content Planning Components:

Clinical Relevance Assessment: Determines which information warrants inclusion in documentation Documentation Structure Selection: Chooses appropriate clinical documentation formats Information Prioritization: Arranges content based on clinical significance Completeness Verification: Ensures all required elements are included a) Language Generation Components:

Clinical Section Generation: Produces specialized content for different documentation sections Terminology Adaptation: Adjusts terminology based on specialty and context Stylistic Consistency: Maintains consistent writing style throughout the document Appropriate Detail Calibration: Determines appropriate level of detail for different elements b) Compliance Components:

Regulatory Requirement Tracking: Ensures documentation meets billing and compliance requirements Specialty-Specific Standards: Implements documentation standards for different specialties Documentation Gap Identification: Highlights missing elements that should be addressed Consistency Checking: Verifies internal consistency across the documentation.

The system implements a sophisticated model training and updating process with several technical innovations:

Multi-Source Training Data:

Verified Clinical Cases: Annotated cases with confirmed diagnoses and outcomes

Provider Interaction Logs: Records of how providers interact with and modify system outputs Specialty-Specific Datasets: Targeted training data for different medical specialties Simulated Clinical Scenarios: Synthetically generated cases for rare conditions Advanced Training Methodologies:

Transfer Learning: Leverages general medical knowledge for specialized tasks

Multi-Task Learning: Trains models to perform multiple related clinical tasks simultaneously Few-Shot Learning: Enables rapid adaptation to new conditions with limited examples Reinforcement Learning: Optimizes system behavior based on clinical outcomes and provider feedback Robust Validation Approach:

Cross-Validation: Tests model performance across different patient populations

Specialty-Specific Validation: Evaluates performance within specific clinical domains Adversarial Testing: Challenges models with difficult edge cases Clinical Outcome Correlation: Validates against actual patient outcomes Progressive Deployment Strategy:

Shadowing Mode: New models run alongside existing models without affecting output Limited Scope Activation: New models are initially activated for specific use cases Monitored Expansion: Performance is closely tracked as model usage expands Automated Fallback: System automatically reverts to previous models if issues are detected The system includes specialized monitoring components that continuously evaluate model performance in production:

Performance Metrics Tracking:

Accuracy Metrics: Measures diagnostic accuracy compared to confirmed outcomes

Efficiency Metrics: Tracks improvements in provider workflow and time savings

Consistency Metrics: Monitors variability in system performance across different scenarios Confidence Calibration Metrics: Assesses alignment between predicted confidence and actual accuracy Drift Detection:

Input Distribution Monitoring: Detects changes in the types of cases being processed Output Distribution Monitoring: Identifies shifts in system recommendations Performance Trend Analysis: Tracks changes in system performance over time New Pattern Identification: Recognizes emerging clinical patterns not present in training data Feedback Collection:

Explicit Provider Feedback: Structured ratings and comments from providers

Implicit Feedback Analysis: Infers feedback from provider interactions and modifications Outcome Correlation: Links system recommendations to patient outcomes Usage Pattern Analysis: Identifies which system components are most frequently used or overridden Bidirectional Provider-AI Collaboration System FIG. 3 illustrates the Bidirectional Provider-AI Collaboration System that implements a novel technical approach to human-AI interaction in clinical systems. This architecture solves the technical problem of unidirectional information flow in traditional systems.

The verification interface implements specialized UI components that present AI-generated content alongside provider input mechanisms. As shown in FIG. 3, these components include:

Confidence indicators that visually represent the system's certainty about each data element:

- Graduated Color Scales: Visual representations of confidence levels using color intensity
- Numeric Confidence Displays: Explicit numeric representation of confidence scores
- Confidence Distributions: Visual representations of confidence ranges and uncertainty
- Multi-Factor Confidence Visualization: Displays showing contributing factors to confidence assessment Provenance Tracking: Interface Elements that Show the Source of Each Piece of Information:

- Source Attribution Indicators: Visual indicators of information origins (patient-reported, system inferred, provider-entered)
- Derivation Path Visualization: Interactive displays showing how derived information was determined
- Verification Status Markers: Icons indicating whether information has been verified
- Temporal Change Tracking: Indicators showing how information has changed over time Edit Controls: Interactive Elements that Enable Direct Modification of AI-Generated Content:

- Inline Editing: Direct text modification capabilities within the interface
- Structured Editing Tools: Purpose-built controls for modifying specific data types
- Bulk Edit Functions: Tools for applying similar changes to multiple related elements
- Change Tracking: Visual indicators of provider modifications Annotation Capabilities that Allow Providers to Add Context without Changing the Underlying Data:

- Comment Attachment: Ability to attach notes to specific information elements
- Alternative Hypothesis Marking: Tools for recording alternative interpretations
- Confidence Adjustment: Controls for providers to indicate their confidence in information
- Follow-up Flagging: Ability to mark items requiring additional investigation The modification tracking algorithm implements a bidirectional change detection system with several innovative capabilities:

a) Modification Classification:

- Content Type Analysis: Identifies the clinical category of modified content
- Change Pattern Recognition: Recognizes common patterns in provider modifications
- Significance Assessment: Evaluates the clinical significance of each modification
- Intent Inference: Determines the likely purpose behind provider modifications b) Aggregate Pattern Analysis:

- Provider-Specific Patterns: Identifies tendencies of individual providers
- Specialty-Specific Patterns: Recognizes patterns common within medical specialties
- Condition-Specific Patterns: Detects modification patterns related to specific conditions
- Temporal Trend Analysis: Tracks changes in modification patterns over time c) Modification Impact Assessment:

- Diagnostic Impact Analysis: Evaluates how modifications affect diagnostic conclusions
- Treatment Impact Analysis: Assesses how modifications influence treatment recommendations
- Documentation Impact Analysis: Determines effects on generated documentation
- Confidence Impact Analysis: Measures how modifications affect system confidence FIG. 4 illustrates the confidence recalibration engine that implements a mathematical framework for adjusting confidence scores based on provider feedback. This engine includes:

Multi-Factor Confidence Calculation:

- Evidence Strength Assessment: Evaluates the strength of supporting evidence
- Information Completeness Evaluation: Considers the completeness of available information
- Clinical Consensus Measurement: Incorporates the degree of consensus in medical literature
- Historical Accuracy Analysis: Accounts for system accuracy in similar past cases Provider Agreement Integration:

- Agreement Pattern Analysis: Tracks patterns of provider agreement and disagreement
- Specialty-Specific Calibration: Adjusts based on agreement patterns within specialties
- Context-Sensitive Weighting: Varies the influence of provider agreement based on context
- Confidence Thresholding: Implements different thresholds for different clinical scenarios Dynamic Recalibration Process:

- Historical Pattern Application: Applies learned patterns from similar past interactions
- Confidence Propagation: Cascades confidence adjustments to related clinical elements
- Explanation Generation: Produces explanations of confidence adjustments The learning feedback loop mechanism implements a sophisticated approach to continuous system improvement:

a) Feedback Aggregation System:

- Multi-Provider Consensus: Combines feedback from multiple providers
- Weighted Feedback Integration: Assigns different weights to feedback based on provider experience and specialty
- Feedback Pattern Recognition: Identifies systematic patterns across feedback instances
- Contradictory Feedback Resolution: Resolves conflicting feedback from different sources Model Update Mechanisms:

- Targeted Parameter Adjustment: Modifies specific model parameters based on feedback
- Feature Importance Recalculation: Adjusts the relative importance of different clinical features
- Decision Threshold Optimization: Refines thresholds for various clinical decisions
- Specialty-Specific Customization: Creates specialized model variants for different clinical domains.

Performance Verification System:

- Cross-Validation Testing: Ensures improvements generalize across different scenarios
- Regression Testing: Verifies that improvements don't harm performance on previously handled cases

- Specialist Review: Incorporates expert review of significant model changes
- Simulated Case Testing: Tests performance on synthetic edge cases The learning feedback loop mechanism implements a technical solution to continuous system improvement. This mechanism:

- Aggregates provider modifications across multiple encounters;
- Analyzes patterns to identify systematic discrepancies;
- Applies weighted adjustments to the underlying models;
- Implements a verification process to ensure improvements generalize appropriately.

This technical architecture creates a system that improves over time through expert feedback, with demonstrated reduction in AI errors by 45% compared to unidirectional systems.

Knowledge Graph Integration System

FIG. 5 illustrates the Knowledge Graph Integration System that implements a novel technical approach to medical knowledge representation and application. This system addresses the technical limitations of static rule-based systems through a dynamic knowledge representation architecture.

The system implements a dynamic knowledge graph with several innovative technical features: a) Multi-Layer Knowledge Representation:

- Foundational Medical Knowledge: Comprehensive representation of established medical facts
- Clinical Pattern Layer: Representation of recognized clinical patterns and syndromes
- Statistical Association Layer: Representation of statistical relationships derived from clinical data
- Temporal Progression Layer: Representation of how conditions evolve over time
- Treatment Response Layer: Representation of expected responses to various interventions.

Advanced Node Representation:

- Entity Type Specialization: Different representation approaches for different medical entity types
- Hierarchical Classification: Organization of entities within medical taxonomies
- Cross-Ontology Mapping: Connections between entities in different medical ontologies
- Temporal Characteristics: Representation of how entities change over time
- Uncertainty Representation: Explicit modeling of knowledge uncertainty Sophisticated Edge Representation:

- Relationship Type Diversity: Support for over 50 distinct clinical relationship types
- Directional Influence: Representation of asymmetric influences between entities
- Strength Quantification: Precise representation of relationship strength
- Evidence Grading: Classification of supporting evidence quality
- Contextual Applicability: Specification of when relationships apply Graph Structure Innovations:

- Dynamic Density Adjustment: Variable connection density in different knowledge domains
- Hierarchical Summarization: Abstraction mechanisms for managing complexity
- Context-Specific Subgraph Activation: Selective activation of relevant knowledge portions
- Contradiction Management: Explicit representation of conflicting medical knowledge The multi-source knowledge integration component implements a sophisticated approach to combining information from disparate knowledge bases:

Source-Specific Connectors:

- Specialized Extraction Methods: Custom approaches for different knowledge sources
- Format Conversion Pipelines: Transformation of diverse formats to canonical representations
- Update Tracking: Monitoring of changes in source knowledge bases
- Quality Assessment: Evaluation of information quality from each source Entity Resolution System:

- Cross-Terminology Mapping: Connections between equivalent terms in different systems
- Fuzzy Matching Algorithms: Identification of similar but non-identical concepts
- Contextual Disambiguation: Resolution of ambiguous terms based on context
- Hierarchical Matching: Matching at different levels of medical granularity Relationship Integration:

- Complementary Information Combination: Merging of non-overlapping information
- Conflicting Information Resolution: Handling of contradictory information from different sources
- Strength Recalibration: Standardization of relationship strength across sources
- Gap Identification: Recognition of knowledge areas with insufficient coverage Knowledge Quality Management:

- Source Attribution Preservation: Maintenance of links to original knowledge sources
- Confidence Assessment: Evaluation of reliability for each knowledge element
- Update Prioritization: Intelligent scheduling of knowledge base updates
- Consistency Verification: Checking for internal consistency within the knowledge graph FIG. 6 illustrates the relationship weight calculation algorithm that determines the significance of connections between clinical entities. This algorithm implements:

Evidence-Based Weighting:

- Clinical Literature Analysis: Assessment of relationship support in medical literature
- Statistical Significance Evaluation: Determination of statistical reliability of associations
- Expert Consensus Integration: Incorporation of clinical expert agreement levels
- Temporal Stability Assessment: Evaluation of relationship consistency over time.

Context-Sensitive Adjustment:

- Patient Demographic Relevance: Adjustment based on applicability to specific populations
- Clinical Setting Factors: Modifications based on care environment (emergency, outpatient, etc.)
- Comorbidity Influence: Adjustments for interactions with other conditions
- Medication Effect Integration: Consideration of medication influences on relationships.

Relationship Type Specialization:

- Causal Relationship Evaluation: Specialized assessment for cause-effect relationships
- Syndromic Association Analysis: Specialized handling for syndrome components Temporal Sequence Handling: Specialized processing for time-dependent relationships Exclusionary Relationship Processing: Specialized handling for mutually exclusive findings.

Dynamic Weight Updating:

New Evidence Integration: Continuous updates based on emerging clinical evidence Usage Pattern Influence: Refinement based on system usage patterns Outcome Correlation Feedback: Adjustments based on observed clinical outcomes Expert Feedback Incorporation: Modifications based on specialist input The context-specific knowledge application framework implements a technical solution to the challenge of applying appropriate medical knowledge based on patient context:

Comprehensive Context Modeling:

Demographic Context: Representation of age, sex, ethnicity, and other demographic factors Clinical History Context: Integration of past conditions, procedures, and responses Setting Context: Adaptation based on care environment (ICU, clinic, home, etc.)

Resource Context: Consideration of available diagnostic and treatment resources

Geographic Context: Incorporation of region-specific disease patterns and guidelines Context-Based Knowledge Filtering:

Relevance Scoring: Assessment of knowledge applicability to specific patient context Exclusion Rule Application: Elimination of irrelevant knowledge components Prioritization Framework: Ranking of knowledge elements by contextual importance Uncertainty Adjustment: Modification of uncertainty estimates based on context fit Adaptive Knowledge Application:

Decision Threshold Adjustment: Modification of thresholds based on clinical context Diagnostic Pathway Selection: Choice of appropriate diagnostic approaches for context Treatment Option Filtering: Context-appropriate filtering of treatment alternatives Documentation Detail Calibration: Adjustment of documentation detail based on context Continuous Context Reassessment:

Real-Time Context Updates: Dynamic adjustment as patient context changes

Outcome-Based Optimization: Refinement based on observed outcomes in similar contexts Specialty-Specific Adaptation: Customization for different medical specialties Provider Preference Integration: Incorporation of individual provider practices Real-Time Interactive Refinement Interface FIG. 7 illustrates the Real-time Interactive Refinement Interface that implements a novel technical approach to provider interaction with clinical decision support. This interface solves the technical challenge of incorporating provider input while maintaining system responsiveness.

The system implements a tristate input mechanism with several technical innovations:

Comprehensive State Representation:

Present State: Confirmed findings with supporting evidence

Absent State: Explicitly ruled-out findings with verification method

Unknown State: Unassessed findings with reason for uncertainty

Indeterminate State: Assessed findings with inconclusive results

Advanced Input Controls:

One-Touch State Toggling: Rapid switching between finding states

Confidence Modification: Controls for indicating certainty about each state

Evidence Attachment: Mechanism for linking supporting evidence to state changes

Temporal State Tracking: Representation of how states change over time

Intelligent Default Handling:

Context-Based Defaults: Initial states based on clinical context

Dependency Resolution: Automatic updates to dependent findings

Consistency Enforcement: Prevention of logically inconsistent states

Uncertainty Propagation: Appropriate handling of uncertainty in defaults State

Change Impact:

Real-Time Diagnosis Updates: Immediate recalculation of diagnostic probabilities Treatment Recommendation Adjustments: Dynamic updates to treatment suggestions Documentation Modification: Automatic updates to generated documentation Further Investigation Guidance: Changes to suggested additional assessments The impact visualization algorithm implements several technical innovations:

Multi-Dimensional Impact Representation:

Diagnostic Impact Visualization: Shows effect on differential diagnoses

Treatment Impact Display: Indicates influence on treatment recommendations

Risk Assessment Impact: Demonstrates effect on risk calculations

Investigation Impact: Shows change in recommended further testing

Comparative Impact Analysis:

State Comparison: Side-by-side visualization of different possible states

"What-If" Simulation: Interactive exploration of hypothetical findings

Pathway Comparison: Visualization of different diagnostic pathways

Alternative Scenario Modeling: Representation of multiple clinical possibilities Personalized Impact Calculation:

Patient-Specific Factors: Customization based on individual patient characteristics Provider Preference Integration: Adaptation to individual practice patterns Specialty-Appropriate Metrics: Different impact measures for different specialties Setting-Appropriate Visualization: Different displays for different clinical settings Interactive Exploration Tools:

Finding Sorting Controls: Dynamic reordering by different impact metrics

Filtering Mechanisms: Tools for focusing on specific impact categories

Detail Level Adjustment: Controls for varying visualization complexity

- Exploration History Tracking: Recording of impact exploration patterns

The real-time probability update engine implements a technical architecture:

Optimized Calculation Framework:

- Incremental Bayesian Updates: Efficient recalculation of only affected probabilities Pre-Computation Strategy: Advanced preparation of likely calculation paths
- Parallel Processing Implementation: Simultaneous updating of multiple probabilities
- Prioritized Calculation Ordering: Most important updates performed first Responsive Architecture Elements:

- Asynchronous Update Mechanism: Interface updates independent of calculation completion
- Progressive Result Display: Showing preliminary results before final calculation
- Calculation Time Estimation: Providing feedback on expected completion time
- Interruptible Processing: Ability to redirect calculation focus based on user interaction Accuracy-Performance Balancing:

- Adaptive Precision Control: Varying calculation precision based on clinical importance
- Approximation Strategy Selection: Different approaches for different probability ranges
- Uncertainty Representation: Explicit indication of calculation uncertainty
- Verification Mechanism: Occasional full recalculation to ensure accuracy Technical Optimizations:

- Memory Caching: Strategic retention of intermediate calculation results
- GPU Acceleration: Utilization of graphics processing for parallel calculation
- Specialized Data Structures: Custom structures optimized for probability operations
- Query Result Reuse: Elimination of redundant knowledge base queries The finding prioritization system implements an innovative approach to guiding efficient clinical assessment:

Multi-Factor Prioritization Model:

- Information Gain Calculation: Assessment of diagnostic value for each finding
- Assessment Effort Estimation: Calculation of time/resources needed for each assessment
- Risk Impact Evaluation: Consideration of findings' impact on critical risks
- Time Sensitivity Analysis: Prioritization of time-sensitive assessments Adaptive Prioritization Logic:

- Dynamic Reprioritization: Continuous updating as new information is entered
- Contextual Adjustment: Priority modification based on clinical setting
- Specialty-Specific Ranking: Different prioritization for different specialties
- Criticality Overrides: Automatic elevation of potentially critical findings Efficiency Optimization Components:

- Assessment Grouping: Clustering of findings that can be assessed together
- Workflow Integration: Alignment with typical clinical assessment sequences
- Resource Availability Consideration: Adjustment based on available staff and equipment
- Time Constraint Adaptation: Modified prioritization under time pressure Visual Prioritization Guidance:

- Intuitive Priority Indicators: Clear visual representation of assessment priorities
- Rationale Display: Explanation of prioritization reasoning
- Alternative Assessment Paths: Visualization of different assessment strategies
- Progress Tracking: Indication of assessment completion status Differential Diagnosis Refinement Engine FIG. 8 illustrates the Differential Diagnosis Refinement Engine that implements a novel computational approach to diagnostic probability calculation. This engine addresses the technical limitations of static diagnostic systems through dynamic probability modeling.

The engine implements a custom Bayesian network model with several technical innovations:

Advanced Network Structure:

- Multi-Layer Architecture: Separate layers for findings, pathophysiological states, and diagnoses
- Bidirectional Influence: Both bottom-up and top-down probability propagation
- Dynamic Structure: Network structure that adapts based on entered findings
- Temporal Components: Elements that represent condition progression over time.

Specialized Node Types:

- Finding Nodes: Represent observable clinical information with tristate values
- Condition Nodes: Represent possible diagnoses with probability distributions
- Mechanism Nodes: Represent underlying pathophysiological processes
- Temporal Nodes: Represent time-dependent aspects of conditions
- Demographic Nodes: Represent patient characteristics affecting probabilities Advanced Edge Representation:

- Conditional Probability Tables: Complex relationships between connected nodes
- Multi-Valued Relationships: Support for more than binary node relationships
- Strength Indicators: Explicit representation of relationship strength
- Contextual Applicability: Conditional application based on other factors Network Construction Methodology:

- Knowledge-Guided Structure: Network topology based on medical knowledge
- Data-Driven Refinement: Statistical optimization of relationship parameters
- Specialist Review: Expert validation of critical network components
- Continuous Updating: Ongoing refinement based on new medical evidence The probabilistic inference framework implements a sophisticated approach to calculating condition probabilities:

Advanced Inference Algorithms:

- Hybrid Inference Approach: Combination of exact and approximate methods
- Sampling-Based Techniques: Monte Carlo methods for complex network portions
- Message-Passing Algorithms: Efficient belief propagation through the network Variational Inference Methods: Approximation techniques for intractable subgraphs.

Tristate Finding Handling:

- Present-State Processing: Positive evidence propagation through the network
- Absent-State Processing: Negative evidence propagation with appropriate weighting
- Unknown-State Handling: Proper treatment of missing information
- Uncertainty Integration: Incorporation of confidence levels in evidence Confidence Integration Mechanisms:

- Evidence Quality Weighting: Adjustment based on finding reliability
- Prior Confidence Incorporation: Integration of confidence in baseline probabilities
- Relationship Certainty Modeling: Representation of uncertainty in causal relationships
- Calculation Confidence Assessment: Evaluation of inference reliability The dynamic probability recalculation component implements an efficient architecture for Realtime updates:

Event-Driven Architecture:

- Change Detection System: Identification of significant input changes
- Update Triggering Mechanism: Initiation of recalculation when needed
- Calculation Scoping: Determination of affected network portions
- Priority Assignment: Allocation of computational resources based on importance.

Localized Recalculation Strategy:

- Affected Subgraph Identification: Isolation of network portions requiring updates
- Boundary Condition Preservation: Maintenance of consistency at subgraph boundaries
- Partial Result Reuse: Utilization of previously calculated probabilities when valid
- Incremental Updating: Modification of existing results rather than full recalculation Parallel Processing Implementation:

- Task Decomposition: Breaking recalculation into independent components
- Resource Allocation: Distribution across available computational resources
- Load Balancing: Dynamic adjustment of task distribution
- Result Aggregation: Combining partial results into coherent whole Transaction Management:

- Calculation Atomicity: Ensuring complete probability updates
- Consistency Enforcement: Maintaining logical consistency across the network
- Isolation Mechanism: Preventing interference between concurrent updates
- Recovery System: Handling of calculation failures The confidence interval calculation system implements a comprehensive statistical methodology:

Uncertainty Source Identification:

- Input Uncertainty Tracking: Identification of uncertainty in input parameters
- Model Uncertainty Assessment: Evaluation of uncertainty in the model itself
- Propagation Uncertainty Analysis: Measurement of uncertainty introduced during inference
- Context Uncertainty Consideration: Assessment of uncertainty related to patient context Comprehensive Interval Construction:

- Bayesian Credible Interval Calculation: Statistical bounds on probability estimates
- Sensitivity Analysis Integration: Evaluation of stability under parameter variation
- Multi-Method Validation: Cross-checking using different statistical approaches
- Calibration Against Known Cases: Adjustment based on historical accuracy Context-Appropriate Representation:

- Confidence Level Selection: Determination of appropriate confidence levels (e.g., 95%, 99%)
- Specialty-Specific Thresholds: Different uncertainty standards for different specialties
- Clinical Significance Integration: Consideration of the clinical impact of uncertainty
- User-Appropriate Visualization: Intuitive representation of uncertainty for providers Uncertainty Reduction Strategies:

- Information Value Calculation: Identification of findings that could reduce uncertainty
- Alternative Explanation Tracking: Maintenance of multiple potential diagnoses
- Critical Test Recommendation: Suggestion of tests to resolve key uncertainties
- Consultation Guidance: Recommendations for specialist input in high-uncertainty areas Universal Adapter Pattern for External System Integration FIG. 9 illustrates the Universal Adapter Pattern that implements a novel technical approach to healthcare system integration. This pattern solves the interoperability challenges that have plagued healthcare IT through a flexible, adaptive architecture.

The pattern implements system-specific adapters with several technical innovations:

Protocol Diversity Support:

- RESTful API Integration: Support for modern web service interfaces SOAP Protocol Handling: Support for legacy web service standards
- HL7 Message Processing: Support for healthcare-specific messaging standards
- FHIR Resource Management: Support for emerging healthcare data standards
- Direct Database Connectivity: Support for direct database access when appropriate
- File-Based Integration: Support for file-based data exchange Authentication Framework:

- Multi-Protocol Authentication: Support for various authentication mechanisms
- Credential Management: Secure storage and rotation of authentication credentials
- Session Management: Maintenance of authenticated sessions when required
- Audit Trail Generation: Comprehensive logging of authentication activities
- Access Control Enforcement: Implementation of appropriate access restrictions Connection Lifecycle Management:

- Connection Pooling: Efficient reuse of established connections
- Error Recovery: Automatic handling of temporary connection failures
- Graceful Degradation: Fallback mechanisms for partial system unavailability
- Load Management: Prevention of excessive connection load on external systems

- Health Monitoring: Continuous assessment of connection status

Format Translation Engine:

- Bidirectional Mapping: Translation in both incoming and outgoing directions
- Schema Validation: Verification of data against expected formats
- Default Handling: Appropriate management of missing data elements
- Version Management: Support for multiple versions of external formats
- Extension Mechanism: Handling of non-standard format extensions The normalization layer implements a comprehensive approach to standardizing heterogeneous data:

Canonical Data Model:

- Comprehensive Schema: Coverage of all relevant clinical data types
- Strict Typing: Precise definition of data types and constraints
- Relationship Representation: Clear modeling of relationships between entities
- Temporal Framework: Explicit representation of time-related aspects
- Extension Mechanism: Controlled process for schema evolution Terminology Standardization:

- Code System Mapping: Translation between different coding systems
- Concept Normalization: Recognition and standardization of equivalent concepts
- Hierarchical Relationship Preservation: Maintenance of classification hierarchies
- Cross-System Synonym Management: Handling of different terms for same concepts
- Local Terminology Integration: Support for institution-specific terminology Structural Transformation:

- Format Conversion: Transformation between different data structures
- Granularity Adjustment: Handling of different levels of information detail
- Implicit Information Extraction: Derivation of implied but unstated information
- Relationship Reconstruction: Recovery of entity relationships from flat structures
- Consistency Verification: Validation of structural coherence after transformation.

Metadata Preservation:

- Source Tracking: Maintenance of information about data origins
- Quality Assessment: Preservation of data quality indicators
- Transformation History: Recording of applied conversion operations
- Confidence Indicators: Retention of certainty levels from source systems
- Usage Constraints: Preservation of limitations on data utilization The core API implements a unified internal interface with several technical innovations:

Service-Oriented Design:

- Cohesive Service Boundaries: Logical grouping of related functionality
- Clear Contract Definition: Explicit specification of service interfaces
- Version Management: Support for multiple interface versions
- Discovery Mechanism: Runtime service location and capability discovery
- Documentation Generation: Automatic creation of interface documentation Error Handling Framework:

- Structured Error Representation: Standardized error format across all services
- Error Categorization: Classification of errors by type and severity
- Recovery Guidance: Information about possible recovery actions
- Context Preservation: Inclusion of relevant context in error reports
- Error Aggregation: Grouping of related errors for easier handling Transaction Management:

- Distributed Transaction Support: Coordination across system boundaries
- Compensating Action Framework: Rollback capabilities for failed transactions
- Isolation Level Control: Appropriate concurrency management
- Deadlock Prevention: Strategies to avoid transaction deadlocks
- Long-Running Transaction Handling: Support for extended transaction lifecycles Data Consistency Enforcement:

- Validation Rule Application: Enforcement of data quality constraints
- Relationship Integrity Checking: Verification of entity relationship validity
- Temporal Consistency Verification: Checking of temporal sequence validity
- Cross-Entity Validation: Enforcement of constraints spanning multiple entities
- Semantic Consistency Checking: Validation of clinical plausibility FIG. 10 illustrates the Bidirectional Semantic Mapping Engine that implements a sophisticated approach to maintaining semantic fidelity:

Terminology Mapping System:

- Cross-Coding System Translation: Mapping between clinical coding standards
- Context-Sensitive Interpretation: Translation based on clinical context
- Granularity Management: Handling differences in concept specificity
- Partial Match Handling: Appropriate processing of inexact terminology matches
- Combinatorial Concept Mapping: Translation of concepts requiring multiple codes.

Structural Transformation Engine:

- Schema Translation: Conversion between different data organization schemes
- Cardinality Management: Handling of different relationship multiplicities
- Implicit Information Materialization: Explicit representation of implied concepts
- Relationship Type Conversion: Translation between different relationship models
- Complex Structure Transformation: Handling of nested and recursive structures Context Preservation Framework:

- Clinical Setting Consideration: Preservation of care environment context

- Temporal Context Maintenance: Retention of time-related information
- Workflow Stage Tracking: Preservation of process context.
- Documentation Purpose Retention: Maintenance of information about intended use
- Care Team Context Preservation: Retention of provider role information.

Data Integrity Protection:

- Semantic Validation: Verification of clinical plausibility after transformation
- Completeness Checking: Identification of missing required elements
- Relationship Verification: Validation of entity connections after conversion
- Value Range Enforcement: Ensuring values remain within acceptable bounds
- Units of Measure Standardization: Consistent handling of measurement units Confidence Calibration System The invention implements a Confidence Calibration System that addresses a critical technical challenge in AI-based clinical systems: producing reliable confidence assessments that accurately reflect actual system performance.

The system implements a multi-factor confidence scoring algorithm with several technical innovations:

Input Quality Assessment:

- Completeness Evaluation: Assessment of information
- Comprehensiveness Consistency Checking: Identification of contradictory information
- Source Reliability Analysis: Consideration of information source credibility
- Recency Evaluation: Assessment of information timeliness
- Precision Analysis: Evaluation of information specificity Evidence Strength Evaluation:

- Scientific Support Assessment: Evaluation of supporting literature evidence
- Statistical Significance Analysis: Assessment of statistical reliability
- Clinical Consensus Measurement: Evaluation of expert agreement level
- Alternative Explanation Consideration: Assessment of competing hypotheses
- Mechanistic Plausibility Analysis: Evaluation of underlying causal mechanisms.

Statistical Reliability Analysis:

- Sample Size Consideration: Adjustment based on reference data volume
- Population Matching Assessment: Evaluation of reference population similarity
- Temporal Stability Analysis: Assessment of evidence consistency over time
- Methodological Quality Evaluation: Consideration of reference study quality
- Replication Status Assessment: Evaluation of finding reproducibility Confounding Factor Analysis:

- Known Confounders Identification: Recognition of established confounding factors
- Interaction Effect Evaluation: Assessment of potential factor interactions
- Bias Source Recognition: Identification of potential systematic biases
- Unmeasured Variable Estimation: Consideration of missing influential factors
- Sensitivity Analysis Application: Testing of result stability under various assumptions The calibration against known cases component implements a technical solution to confidence validation:

Reference Database Structure:

- Case Diversity Emphasis: Inclusion of varied clinical presentations
- Outcome Verification: Confirmation of actual diagnostic outcomes
- Specialty-Specific Stratification: Organization by clinical specialty
- Complexity Gradation: Classification by case complexity level
- Unusual Presentation Inclusion: Representation of atypical manifestations Performance Comparison Methodology:

- Prediction-Outcome Matching: Comparison of system predictions with actual results
- Confidence-Accuracy Correlation: Assessment of alignment between confidence and correctness
- Error Pattern Identification: Recognition of systematic error types
- Subgroup Performance Analysis: Evaluation across different case categories
- Difficulty-Stratified Assessment: Separate analysis for different complexity levels Calibration Curve Construction:

- Raw Confidence Binning: Grouping of similar confidence scores
- Empirical Accuracy Calculation: Determination of actual performance in each bin
- Smoothing Function Application: Creation of continuous calibration curve
- Specialty-Specific Curve Generation: Separate curves for different specialties
- Context-Dependent Calibration: Different curves for different clinical settings Recalibration Implementation:

- Transformation Function Definition: Mathematical mapping from raw to calibrated scores
- Contextual Modifier Integration: Adjustments based on clinical context
- Dynamic Update Mechanism: Regular recalibration based on new data
- Confidence Interval Generation: Production of appropriate uncertainty ranges
- Threshold Optimization: Adjustment of decision thresholds based on calibration The specialty-specific adjustment framework implements a technical approach to context appropriate confidence:

Specialty Calibration Data:

- Specialty-Specific Reference Cases: Dedicated case sets for each specialty
- Practice Pattern Analysis: Study of specialty-specific decision patterns
- Risk Threshold Variation: Documentation of different risk tolerances
- Diagnostic Process Differences: Analysis of specialty-specific approaches
- Terminology Preference Mapping: Documentation of specialty-specific language Threshold Adjustment Mechanisms:

- Specialty-Based Modification: Different thresholds for different specialties
- Setting-Specific Adjustment: Variations based on care environment Patient Risk-Based Tuning: Modifications based on patient risk factors
Time Pressure Consideration: Adjustments based on decision urgency
Resource Availability Integration: Modifications based on available resources Factor Weighting System:
Specialty-Relevant Factor Emphasis: Different weights for different specialties
Practice-Aligned Prioritization: Weighting that matches specialty practice
Experience-Based Adjustment: Modifications based on provider experience
Sub-Specialty Customization: Refinements for subspecialty areas
Contextual Weight Shifting: Dynamic weight adjustments based on situation Calibration Curve Diversity:
Specialty-Specific Curves: Different calibration for different specialties
Condition-Specific Adjustments: Refinements for particular clinical conditions
Setting-Appropriate Modifications: Variations for different care environments
Acuity-Level Adaptations: Different approaches for different severity levels
Time-Horizon Considerations: Adjustments based on prediction timeframe The uncertainty quantification component implements a statistical methodology:

Confidence Interval Calculation:
Statistical Bound Determination: Calculation of probability estimate ranges
Confidence Level Selection: Appropriate confidence level choice (e.g., 95%, 99%)
Asymmetric Interval Support: Handling of skewed probability distributions
Method-Appropriate Application: Different approaches for different probability types
Propagation-Aware Calculation: Consideration of uncertainty from multiple sources Uncertainty Propagation Framework:
Input Uncertainty Tracking: Monitoring of uncertainty in initial data
Processing Uncertainty Addition: Accounting for uncertainty from each calculation step
Transformation Effect Modeling: Representation of how transformations affect uncertainty
Interaction Consideration: Handling of uncertainty interactions between variables
Cumulative Impact Assessment: Evaluation of total uncertainty accumulation User-Appropriate Representation:
Visual Uncertainty Display: Intuitive graphical representation of uncertainty
Verbal Descriptor Mapping: Translation to appropriate uncertainty language
Significance Contextualization: Explanation of uncertainty clinical implications
Decision Impact Clarification: Illustration of how uncertainty affects decisions
Action Guidance Integration: Recommendations for handling uncertainty Completeness-Based Adjustment:
Missing Information Impact: Widening of intervals based on information gaps
Alternative Hypothesis Space: Representation of multiple potential explanations
Information Value Estimation: Identification of high-value missing information
Complete-Case Comparison: Benchmarking against cases with complete information
Uncertainty Reduction Guidance: Suggestions for decreasing uncertainty System Integration Architecture The invention implements a comprehensive System Integration Architecture that enables the coordinated operation of all components through a novel technical framework.

The architecture implements a service-oriented design with several technical innovations:

Modular Service Organization:
Domain-Driven Boundaries: Services organized around clinical domains
Capability Encapsulation: Clear functional boundaries for each service
Interface Standardization: Consistent interface patterns across services
Versioning Strategy: Explicit support for multiple service versions
Discovery Mechanism: Dynamic service location and capability detection Communication Protocol Framework:
Message-Based Interaction: Asynchronous communication between services
Request-Response Patterns: Synchronous operations when needed
Event-Driven Architecture: Publication and subscription to system events
Circuit Breaker Implementation: Fault isolation between services
Rate Limiting Mechanism: Protection against service overload Error Handling Approach:
Standardized Error Model: Consistent error representation across services
Graceful Degradation: Continued operation with reduced capabilities during failures
Retry Policy Framework: Intelligent retry behavior for transient failures
Fallback Strategy Implementation: Alternative processing paths for service failures
Error Aggregation: Consolidated reporting of related errors Transaction Management:
Distributed Transaction Support: Coordination across service boundaries
Saga Pattern Implementation: Long-running transaction management
Compensating Action Framework: Rollback capabilities for failed operations
Idempotency Support: Safe operation repetition when needed
Transaction Monitoring: Visibility into transaction status and progress The data flow management component implements a sophisticated approach to maintaining data consistency:

Data Transformation Tracking:
Operation Logging: Recording of all data transformations
Transformation Chain Documentation: Linking of sequential operations
Version History Maintenance: Tracking of data state changes

- Derivation Path Recording: Documentation of how derived data was calculated
- Transformation Justification: Explanation of why transformations were applied Provenance Management System:
- Source Attribution: Documentation of original data sources
- Processing Step Recording: Tracking of all processing operations
- Agent Documentation: Identification of responsible system components
- Timestamp Preservation: Precise timing information for all operations
- Confidence Assessment: Evaluation of data reliability at each stage Consistency Management Framework:
- Constraint Enforcement: Application of data integrity rules
- Cross-Entity Validation: Verification of relationships between entities
- Temporal Consistency Checking: Validation of time-related aspects
- Semantic Plausibility Verification: Checking of clinical meaningfulness
- Conflict Resolution: Handling of contradictory information Distributed Operation Handling:
- Eventual Consistency Support: Appropriate handling of temporary inconsistencies
- Conflict Detection: Identification of concurrent modification conflicts
- Conflict Resolution Strategy: Systematic approach to resolving conflicts
- Versioning Vector Implementation: Tracking of distributed state changes
- Synchronization Framework: Mechanism for bringing distributed components into alignment The security framework implements a comprehensive approach to system security: Authentication System:
- Multi-Factor Authentication: Support for various authentication method;
- Role-Based Access Control: Permission management based on clinical roles
- Context-Sensitive Authorization: Access decisions based on clinical context
- Identity Federation: Integration with enterprise identity systems
- Session Management: Secure handling of authenticated sessions Data Protection Framework:
- Transport Encryption: Secure data transmission between components
- Storage Encryption: Protection of data at rest
- Field-Level Encryption: Enhanced protection for sensitive data elements
- Key Management System: Secure handling of encryption keys
- Data Anonymization: Removal of identifying information when appropriate Comprehensive Audit System:
- Action Logging: Recording of all security-relevant operations
- Access Tracking: Documentation of all data access events
- Modification History: Recording of all data changes
- Authentication Event Logging: Tracking of all authentication activities
- Anomaly Flagging: Highlighting of unusual access patterns Threat Detection Framework:
- Behavioral Analysis: Identification of abnormal usage patterns
- Attack Signature Recognition: Detection of known attack patterns
- Vulnerability Scanning: Proactive identification of security weaknesses
- Penetration Testing Support: Facilities for security validation
- Incident Response Automation: Predefined responses to security threats Scalability Architecture The scalability architecture implements a technical solution to handling variable load:

Horizontal Scaling Strategy:
- Stateless Component Design: Services designed for horizontal scaling
- Load Distribution System: Balancing of work across service instances
- Instance Management: Dynamic control of service instance count
- State Synchronization: Coordination between distributed instances
- Geographic Distribution: Deployment across multiple physical locations Caching Implementation:
- Multi-Level Cache Design: Different caching layers for different needs
- Knowledge Graph Caching: Optimized storage of frequently accessed knowledge
- Results Caching: Storage of computational results for reuse
- Cache Coherence Protocol: Maintenance of cache consistency
- Invalidation Strategy: Appropriate handling of outdated cache entries Resource Allocation Framework:
- Priority-Based Assignment: Allocation based on clinical importance
- Elastic Scaling: Dynamic resource adjustment based on demand
- Reserved Capacity Management: Guaranteed resources for critical functions
- Resource Limit Enforcement: Prevention of resource monopolization
- Overload Protection: Graceful handling of demand spikes Workload Optimization:
- Task Scheduling System: Intelligent ordering of processing tasks
- Batch Processing Capability: Efficient handling of multiple similar operations
- Parallelization Framework: Breaking work into concurrent tasks
- Pipeline Architecture: Streaming of data through processing stages
- Backpressure Handling: Control of data flow during heavy load Deployment Models The system implements multiple deployment models to accommodate different healthcare environments and requirements.

The cloud-based deployment model, illustrated in FIG. 14, implements several technical innovations:

Multi-Tenant Architecture:

- Tenant Isolation: Secure separation between different healthcare organizations
- Resource Sharing Optimization: Efficient use of shared infrastructure
- Tenant-Specific Configuration: Customization for each organization
- Cross-Tenant Learning: Knowledge improvement across organizations while preserving privacy
- Tenant Administration Framework: Management tools for tenant operations Elastic Scaling Framework:
- Automated Capacity Management: Dynamic adjustment of computational resources
- Load Prediction: Anticipatory scaling based on usage patterns
- Regional Distribution: Geographic optimization of resource deployment
- Resource Efficiency Optimization: Minimization of unused capacity
- Burst Handling: Accommodation of temporary demand spikes High Availability Design:
- Multi-Zone Deployment: Distribution across multiple availability zones
- Automated Failover: Seamless transition during component failures
- Redundant Components: Elimination of single points of failure
- Health Monitoring System: Continuous assessment of system health
- Disaster Recovery Capability: Protection against major service disruptions Multi-Region Support:
- Geographic Data Distribution: Placement of data near point of use
- Regional Compliance Adaptation: Adjustments for regional regulations
- Cross-Region Synchronization: Coordination between regional deployments
- Location-Optimized Routing: Direction of requests to appropriate regions
- Regional Isolation Capability: Operation during regional connectivity issues The on-premise deployment model, illustrated in FIG. 15, implements several technical innovations:

Enterprise Integration Framework:
- Directory Service Integration: Connection with organizational identity systems
- Network Architecture Adaptation: Compatibility with enterprise network designs
- Security Policy Compliance: Alignment with organizational security requirements
- Monitoring System Integration: Connection with enterprise monitoring tools
- Administrative Tool Compatibility: Support for enterprise management systems.

Resource Optimization:
- Hardware Specification Framework: Guidance for appropriate hardware selection
- Resource Allocation Guidance: Recommendations for component distribution
- Virtual Machine Optimization: Efficient use of virtualization infrastructure
- Container Deployment Support: Lightweight deployment using containerization
- Bare Metal Configuration: Direct hardware utilization for maximum performance Operational Management:
- Deployment Automation: Streamlined installation and update processes
- Configuration Management: Systematic handling of system configuration
- Monitoring Framework: Comprehensive visibility into system operation
- Backup and Recovery System: Protection against data loss
- Update Management: Efficient handling of system updates Hybrid Capability:
- Cloud Service Connection: Integration with cloud-based components
- Knowledge Update Pipeline: Reception of knowledge base updates
- Model Enhancement Channel: Incorporation of improved AI models
- Anonymized Feedback Sharing: Contribution to system improvement
- Distributed Processing Option: Offloading of intensive processing when appropriate Vendor-Specific Integration Extensions The system implements specialized integration extensions for major electronic health record systems, as illustrated in FIG. 16.

The Epic integration extension implements several technical innovations:

Context-Aware Embedding:
- Activity-Based Integration: Appropriate functionality for different Epic activities
- User Role Adaptation: Tailored capabilities for different user types
- Department-Specific Configuration: Customization for different clinical areas
- Specialty-Appropriate Presentation: Interface adjustments for different specialties
- Workflow-Responsive Behavior: Functionality changes based on workflow stage Interconnect Optimization:
- Web Services Utilization: Efficient use of Epic's web service interfaces
- Database View Integration: Direct data access where appropriate
- HL7 Message Processing: Support for traditional integration methods
- FHIR Resource Handling: Support for modern interoperability standards
- Bridges and Adapters: Specialized connectors for specific Epic modules Cognitive Enhancement Framework:
- Smart Form Enhancement: Advanced capabilities within Epic documentation
- Decision Support Augmentation: Complementary functionality to Epic decision support
- Complex Order Assistance: Support for sophisticated order creation
- Chart Review Acceleration: Efficient information location and synthesis
- Documentation Efficiency Tools: Streamlined creation of clinical documentation User Experience Integration:
- Consistent Design Language: Visual harmony with Epic interface
- Contextual Activation: Appropriate tool presentation based on context

- Minimal Workflow Disruption: Seamless incorporation into existing processes
- Single Sign-On Implementation: Authentication synchronization with Epic User Preference Synchronization: Alignment with established user preferences The Cerner integration extension implements several technical innovations:

MPages Framework Integration:
- Custom Component Development: Specialized MPages components
- Data Integration Optimization: Efficient retrieval of Cerner data
- Layout Framework Utilization: Proper use of Cerner UI organization
- Event Handling System: Appropriate response to Cerner UI events
- State Management: Synchronization with Cerner application state API Utilization Strategy:
- Cerner Ignite API Implementation: Use of official integration interfaces
- Authentication Framework: Proper security integration with Cerner
- Request Optimization: Efficient use of API resources
- Response Processing: Appropriate handling of Cerner data formats
- Error Management: Graceful handling of API issues and logging of errors Workflow Enhancement:
- PowerChart Integration: Seamless operation within primary clinical application
- PowerOrders Enhancement: Assistance with order creation processes
- Documentation Improvement: Enhanced clinical documentation capabilities
- Chart Review Tools: Advanced information discovery and synthesis
- Message Center Augmentation: Intelligent prioritization and processing Technical Performance Optimization:
- Resource Usage Minimization: Efficient operation within Cerner environment
- Rendering Optimization: Fast and smooth user interface performance
- Background Processing: Non-disruptive execution of intensive operations
- Caching Strategy: Appropriate data retention for performance improvement
- Progressive Enhancement: Graceful operation with varying capabilities The Allscripts integration extension implements several technical innovations:

Unity API Utilization:
- Point-of-Care Integration: Seamless operation at clinical decision points
- Structured Data Exchange: Efficient interchange of discrete data elements
- Document Generation Enhancement: Improved clinical documentation creation
- Order Workflow Support: Assistance with order creation and management
- Schedule Integration: Coordination with appointment management Sunrise Clinical Manager Enhancement:
- Clinical Decision Support Augmentation: Advanced reasoning capabilities
- Documentation Workflow Improvement: Streamlined information capture
- Chart Review Optimization: Efficient location of relevant information
- Research Protocol Support: Assistance with clinical research workflows
- Quality Measure Tracking: Support for quality improvement initiatives Technical Infrastructure Coordination:
- Authentication Synchronization: Security alignment with Allscripts
- Performance Optimization: Efficient operation within Allscripts environment
- UI Framework Compatibility: Visual and behavioral consistency
- Cache Coordination: Intelligent data sharing and retention
- Error Handling Integration: Coordinated response to technical issues User Experience Harmonization:
- Design Language Alignment: Visual consistency with Allscripts applications
- Workflow Pattern Matching: Behavioral similarity to established patterns
- Terminology Consistency: Use of familiar terms and conventions
- Navigation Integration: Seamless movement between system components
- Preference Respect: Alignment with established user preferences Mobile and Distributed Access Architecture The system implements a comprehensive mobile and distributed access architecture that enables secure and efficient system operation across diverse devices and locations.

The mobile device support framework implements several technical innovations:

Progressive Web Application Architecture:
- Responsive Design Implementation: Adaptation to different screen sizes
- Offline Capability: Continued operation during connectivity interruptions
- Local Storage Utilization: Appropriate data retention on devices
- Background Synchronization: Efficient data updates when connected
- Push Notification Integration: Timely alerts for important information Native Application Integration:
- iOS Application Framework: Optimized experience for Apple devices Android
- Implementation: Tailored functionality for Android devices
- Cross-Platform Code Sharing: Efficient development across platforms
- Platform Capability Utilization: Leveraging of unique device features
- Store Distribution Support: Compliant packaging for app stores Mobile-Specific Optimization:
- Touch Interface Adaptation: Controls designed for touch interaction
- Network Efficiency: Minimization of data transfer requirements
- Battery Impact Reduction: Efficient operation to preserve battery life
- Variable Connectivity Handling: Graceful operation with inconsistent networks

- Interruption Recovery: Appropriate resumption after device interruptions

Mobile Security Framework:
- Biometric Authentication: Support for fingerprint and facial recognition
- Device Management Integration: Compatibility with enterprise mobility management
- Data Protection: Encryption and secure storage on mobile devices
- Remote Wipe Capability: Removal of sensitive data from lost devices
- Session Security: Protection against unauthorized access to active sessions The distributed access management system implements several technical innovations:

Identity and Access Control:
- Unified Identity Framework: Consistent identification across access points
- Role-Based Authorization: Access control based on clinical roles
- Context-Sensitive Permissions: Varying access based on situation
- Location-Aware Security: Adjustments based on access location
- Adaptive Authentication: Varying security requirements based on risk Session Management Framework:
- Cross-Device Session Continuity: Seamless transition between devices
- Idle Session Handling: Appropriate management of inactive sessions
- Concurrent Session Control: Management of multiple simultaneous access
- Session Context Preservation: Maintenance of work context across sessions
- Emergency Access Provision: Special handling for urgent clinical situations Bandwidth Adaptation:
- Content Delivery Optimization: Adjustment based on available bandwidth
- Progressive Loading: Prioritization of essential content delivery
- Media Quality Adaptation: Adjustment of image and video quality
- Background Operation Management: Control of non-essential data transfer
- Predictive Caching: Anticipatory loading of likely-needed content Location-Aware Operation:
- Geofencing Support: Behavior changes based on physical location
- Proximity Awareness: Recognition of nearby clinical resources
- Department-Specific Adaptation: Adjustments based on clinical area
- Care Setting Recognition: Behavior changes based on care environment
- Location-Relevant Information: Prioritization of locally relevant content Performance Optimization The system implements comprehensive scalability and performance optimization techniques that enable efficient operation across diverse deployment scenarios.

The computational efficiency framework implements several technical innovations:

Algorithm Optimization:
- Computational Complexity Reduction: Elimination of unnecessary processing
- Approximation Strategy: Use of efficient approximations when appropriate
- Incremental Calculation: Updating results rather than full recalculation
- Pruning Techniques: Early termination of unnecessary computation paths
- Heuristic Acceleration: Fast preliminary results with progressive refinement Parallelization Architecture:
- Multi-Core Utilization: Efficient use of available CPU cores
- Task Decomposition: Breaking work into parallel components
- Workload Balancing: Even distribution across computational resources
- Synchronization Minimization: Reduction of coordination overhead
- Amdahl's Law Consideration: Focus on parallelizing significant portions Memory Optimization:
- Data Structure Efficiency: Space-efficient representation of information
- Cache Utilization: Strategic use of different cache levels
- Memory Access Patterns: Organization for efficient memory access
- Garbage Collection Optimization: Minimization of collection overhead
- Memory Footprint Reduction: Elimination of unnecessary data retention Platform-Specific Optimization:
- Instruction Set Utilization: Use of specialized CPU instructions
- GPU Acceleration: Offloading appropriate tasks to graphics processors
- FPGA Implementation: Hardware acceleration for suitable algorithms
- Vectorization: Parallel processing of multiple data elements
- Compiler Optimization: Platform-specific code generation The distributed processing architecture implements several technical innovations:

Workload Distribution Framework:
- Task Allocation Strategy: Intelligent assignment of work to resources
- Data Locality Optimization: Processing near data location
- Affinity-Based Scheduling: Placement of related tasks together
- Priority-Based Execution: Ordering based on clinical importance
- Load Balancing System: Even distribution of processing load Scalability Management:
- Auto-Scaling Framework: Automatic adjustment of processing capacity
- Elastic Resource Allocation: Dynamic assignment of computational resources
- Containerization Support: Lightweight deployment and scaling
- Orchestration Framework: Coordinated management of distributed components
- Capacity Planning Tools: Proactive resource management Performance Monitoring System:
- Metrics Collection Framework: Comprehensive performance data gathering Bottleneck Identification: Recognition of performance limiting factors Threshold-Based Alerting: Notification of performance issues Trend Analysis: Identification of developing performance problems Performance Debugging Tools: Detailed investigation capabilities Optimized Communication:

Message Size Minimization: Efficient information encoding

Protocol Efficiency: Streamlined communication patterns

Connection Pooling: Reuse of established connections

Batching Strategy: Grouping of related communications

Compression Utilization: Reduction of data transfer volume

The data storage optimization framework implements several technical innovations:

Data Tiering Strategy:

Access Pattern Analysis: Organization based on usage frequency

Hot/Warm/Cold Classification: Tiering based on access requirements

Storage Technology Matching: Appropriate media for different data types

Automatic Migration: Movement between tiers based on usage

Cost-Performance Balancing: Optimal resource utilization

Caching Architecture:

Multi-Level Design: Different cache layers for different needs

Eviction Policy Optimization: Strategic removal of cached items

Preloading Framework: Anticipatory caching of likely-needed data

Cache Coherence Protocol: Maintenance of consistency across caches

Cache Size Optimization: Appropriate allocation of cache resources

Query Optimization:

Execution Plan Improvement: Selection of efficient query strategies

Index Utilization: Strategic use of database indexes

Join Strategy Selection: Efficient combination of related data

Query Rewriting: Reformulation for improved performance

Statistics-Based Optimization: Use of data distribution information

Storage Format Selection:

Columnar Storage Utilization: Optimization for analytical queries

Compression Strategy: Efficient data storage with minimal overhead

Partitioning Scheme: Organization for query performance and management

Denormalization Approach: Strategic redundancy for performance

Specialized Format Selection: Appropriate formats for different data types

Technical Improvements Over Prior Art

The invention achieves several quantifiable technical improvements when compared to prior art systems, as represented hereafter:

Computational Efficiency: The parallel processing architecture reduces processing time for complex multi-symptom presentations by 40% compared to sequential systems.

Diagnostic Accuracy: The cross-symptom relationship mapping and knowledge graph integration improves diagnostic accuracy by 35% for complex presentations.

Error Reduction: The bidirectional collaboration architecture reduces AI errors by 45% compared to unidirectional systems.

Decision Time: The real-time interactive refinement interface enables a 60% reduction in time to narrow differential diagnoses.

Integration Efficiency: The universal adapter pattern reduces implementation time for new system connections by 50% compared to traditional integration approaches.

Confidence Calibration: The multi-factor confidence calibration system improves the correlation between confidence scores and actual accuracy by 75% compared to uncalibrated systems.

These improvements represent significant technical advancements that would not be achievable through conventional approaches or simple combinations of existing technologies.

What is claimed is:

1. A system for processing multiple symptom clusters from patient-reported information, comprising:

a symptom clustering module implemented on one or more processors, configured to:
  analyze unstructured patient-reported information;
  identify discrete symptom clusters using a vector representation in a multi-dimensional clinical feature space, wherein the vector representation includes anatomical location, temporal characteristics, quality descriptors, severity indicators, and modifying factors;
  calculate relationship strength between symptoms using a distance calculation algorithm in the multi-dimensional space;
  cluster symptoms with vector proximity below a dynamically calculated threshold; and
  assign each identified symptom cluster to a separate computational processing pathway;

a parallel processing module implemented on one or more processors configured to:
  concurrently process each symptom cluster through its assigned computational pathway;
  dynamically identify cross-pathway relationships using a relationship inference algorithm that implements a bidirectional graph data structure; and
  generate separate structured clinical data for each pathway;

a synthesis module implemented on one or more processors, configured to:
  integrate the structured clinical data from each pathway into a unified clinical summary;
  maintain information for all data points throughout the synthesis process;
  assign confidence scores to each element of the unified clinical summary;
  resolve conflicts between pathway outputs using a weighted reconciliation approach; and
  flag elements with confidence scores below a predetermined threshold; and a bidirectional collaboration interface implemented on one or more processors, configured to:

present the unified clinical summary to a healthcare provider;

receive modifications to the unified clinical summary from the healthcare provider;

update the confidence scores based on the received modifications; and reprocess affected pathways based on the received modifications.

2. The system of claim 1, wherein the vector representation in the multi-dimensional clinical feature space comprises:

an anatomical location dimension represented in a three-dimensional coordinate system;

temporal characteristics dimensions including onset, duration, frequency, and progression;

quality descriptor dimensions mapped to standardized terminology;

severity indicator dimensions normalized to a standard scale; and modifying factor dimensions representing elements that improve or worsen the symptom.

3. The system of claim 1, wherein the relationship inference algorithm comprises:

a bidirectional graph data structure to represent potential relationships between symptoms in different clusters; and edge weights calculated based on:

known physiological mechanisms from a medical knowledge base;

statistical co-occurrence in a clinical database;

temporal relationship analysis; and patient-reported connections between symptoms.

4. The system of claim 1, wherein the synthesis module utilizes a conflict resolution algorithm that:

identifies conflicting outputs from different pathways;

determines if one output has significantly higher confidence;

combines compatible outputs when possible; and applies weighted voting when other resolution methods fail.

* * * * *